(12) United States Patent
Filippov et al.

(10) Patent No.: US 12,016,918 B2
(45) Date of Patent: Jun. 25, 2024

(54) PEPTIDE-CONTAINING ADJUVANT COMPOUNDS HAVING PEG SPACERS

(71) Applicants: UNIVERSITEIT LEIDEN, Leiden (NL); ACADEMISCH ZIEKENHUIS LEIDEN, Leiden (NL)

(72) Inventors: Dmitri V. Filippov, Leiden (NL); Geoffroy P. P. Gential, Leiden (NL); Gijsbert Van Der Marel, Leiden (NL); Ferry Ossendorp, Leiden (NL)

(73) Assignees: UNIVERSITEIT LEIDEN, Leiden (NL); ACADEMISCH ZIEKENHUIS LEIDEN, Leiden (NL)

( * ) Notice: Subject to any disclaimer, the term of this patent is extended or adjusted under 35 U.S.C. 154(b) by 614 days.

(21) Appl. No.: 16/609,136

(22) PCT Filed: Apr. 25, 2018

(86) PCT No.: PCT/EP2018/060636
§ 371 (c)(1),
(2) Date: Oct. 28, 2019

(87) PCT Pub. No.: WO2018/197582
PCT Pub. Date: Nov. 1, 2018

(65) Prior Publication Data
US 2020/0188512 A1 Jun. 18, 2020

(30) Foreign Application Priority Data
Apr. 27, 2017 (NL) .................................. 2018803

(51) Int. Cl.
*A61K 39/39* (2006.01)
*A61K 47/64* (2017.01)
(Continued)

(52) U.S. Cl.
CPC .............. *A61K 39/39* (2013.01); *A61K 47/64* (2017.08); *C07K 5/0606* (2013.01); *A61K 2039/55516* (2013.01); *A61K 45/06* (2013.01)

(58) Field of Classification Search
None
See application file for complete search history.

(56) References Cited

U.S. PATENT DOCUMENTS

| 6,504,010 | B1 | 1/2003 | Wang et al. |
| 7,425,607 | B2 | 9/2008 | Henderson et al. |
| 2013/0295129 | A1* | 11/2013 | Irvine ................ A61K 39/12 424/283.1 |

FOREIGN PATENT DOCUMENTS

| WO | 9814464 | 4/1998 |
| WO | 0006723 | 2/2000 |

(Continued)

OTHER PUBLICATIONS

Netherland Application No. 2018803, "Priority Search Report", dated Dec. 18, 2017, 7 pages.
(Continued)

*Primary Examiner* — Kevin S Orwig
(74) *Attorney, Agent, or Firm* — Kilpatrick Townsend & Stockton LLP

(57) ABSTRACT

Adjuvant compounds are described, as well as their conjugates comprising peptide antigens or other immunomodulatory moieties. Also described are methods of modulating immune responses in a subject in need thereof, as well as methods of treating cancer, viral or bacterial infections comprising administering the adjuvant compounds or the conjugates to a subject in need thereof.

14 Claims, 6 Drawing Sheets

Specification includes a Sequence Listing.

(51) Int. Cl.
    *C07K 5/062*    (2006.01)
    *A61K 39/00*    (2006.01)
    *A61K 45/06*    (2006.01)

(56) References Cited

FOREIGN PATENT DOCUMENTS

| WO | 02070006 | 9/2002 |
| WO | 2004058159 A2 | 7/2004 |
| WO | 2006104389 | 10/2006 |
| WO | 2008118017 | 10/2008 |
| WO | 2008147186 | 12/2008 |
| WO | 2008147187 | 12/2008 |
| WO | 2014113634 | 7/2014 |
| WO | 2016103192 A1 | 6/2016 |
| WO | 2016154586 A1 | 9/2016 |

OTHER PUBLICATIONS

International Application No. PCT/EP2018/060636, International Preliminary Report on Patentability, dated Nov. 7, 2019, 10 pages.
International Application No. PCT/EP2018/060636, International Search Report and Written Opinion, dated Jul. 18, 2018.
Salunke et al., 2013, "Design and development of stable, water-soluble, human Toll-like receptor 2 specific monoacyl lipopeptides as candidate vaccine adjuvants." Journal of Medicinal Chemistry 56(14): 5885-5900.
Agnihotri et al., Structure-Activity Relationships in Toll-like Receptor 2-Agonists Leading to Simplified Monoacyl Lipopeptides, Journal of Medicinal Chemistry, 2011, 54(23): 8148-8160.
Buckanovich et al., Endothelin B Receptor Mediates the Endothelial Barrier to T Cell Homing to Tumors and Disables Immune Therapy, Nature Medicine, 2008, 14(1): 28-36.
Bundgaard, (C) Means to Enhance Penetration: (1) Prodrugs as a Means to Improve the Delivery of Peptide Drugs, Advanced Drug Delivery Reviews, 1992, 8(1): 1-38.
Carter et al., Coupling Strategies for the Synthesis of Peptide-Oligonucleotide Conjugates for Patterned Synthetic Biomineralization, Journal of Nucleic Acids, 2011, 2011: 1-8.
Ishikawa et al., Biochemical and Pharmacological Profile of a Potent and Selective Endothelin B-Receptor Antagonist, BQ-788, Proceedings of the National Academy of Sciences of the United States of America, 1994, 91(11): 4892-4896.
Kakeya, Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-Methoxyiminoacetamido]-3-Methyl-3-Cephem-4-Carboxylic Acid, Chemical and Pharmaceutical Bulletin, 1984, 32(2): 692-698.
Khan et al., Chirality of TLR-2 Ligand Pam3CysSK4 in Fully Synthetic Peptide Conjugates Critically Influences the Induction of Specific CD8+ T-Cells, Molecular Immunology, 2009, 46(6): 1084-1091.
Krogsgaard-Larsen et al., A Textbook of Drug Design and Development, 3$^{rd}$ Edition, Taylor & Francis Inc., 2002, 666 pages.
Nielsen et al., Sequence-Selective Recognition of DNA by Strand Displacement with a Thymine-Substituted Polyamide, Science, 1991, 254: 1497-1500.
Salunke et al., Structure-Activity Relationships in Human Toll-like Receptor 2-Specific Monoacyl Lipopeptides, Journal of Medicinal Chemistry, 2012, 55(7): 3353-3363.
Salunke et al., "Design and Development of Stable, Water-Soluble, Human Toll-like Receptor 2 Specific Monoacyl Lipopeptides as Candidate Vaccine Adjuvants", Journal of Medicinal Chemistry, 2013, 56(14): 1-36.
Winzler et al., Maturation Stages of Mouse Dendritic Cells in Growth Factor-Dependent Long-Term Cultures, Journal of Experimental Medicine, 1997, 185(2): 317-328.
Zom et al., Efficient Induction of Antitumor Immunity by Synthetic Toll-like Receptor Ligand-Peptide Conjugates, Cancer Immunology Research, 2014, 2(8): 756-764.
Zom et al., TLR Ligand-Peptide Conjugate Vaccines: Toward Clinical Application, Advances in Immunology, 2012, 114: 177-201.
Zom et al., Two in One: Improving Synthetic Long Peptide Vaccines by Combining Antigen and Adjuvant in One Molecule, OncoImmunology, 2014, 3(7): e947892-1-e947892-3.
International Application No. PCT/EP2018/060636, International Preliminary Report on Patentability dated Nov. 7, 2019, 8 pages.

* cited by examiner

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial sequence
<220> FEATURE:
<223> OTHER INFORMATION: MHC 1 epitope

<400> SEQUENCE: 1

Asp Glu Val Ser Gly Leu Glu Gln Leu Glu Ser Ile Ile Asn Phe Glu
1               5                   10                  15

Lys Leu
```

```
<210> SEQ ID NO 2
<211> LENGTH: 6
<212> TYPE: PRT
<213> ORGANISM: Artificial Sequence
<220> FEATURE:
<223> OTHER INFORMATION: Synthetic lipopeptide
<220> FEATURE:
<221> NAME/KEY: SITE
<222> LOCATION: (1)..(1)
<223> OTHER INFORMATION: Modified Cys residue:
      S-[2,3-Bis(palmitoyloxy)-(2-RS)-propyl]-N-palmitoyl]-Cys

<400> SEQUENCE: 2

Cys Ser Lys Lys Lys Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic lipopeptide
<220> FEATURE:
<221> NAME/KEY: site
<222> LOCATION: (1)..(1)
<223> OTHER INFORMATION: Modified Cys: N-acetylated and
      S-(EtOC(O)C15H31)

<400> SEQUENCE: 3

Cys Ser Lys Lys Lys Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic lipopeptide
<220> FEATURE:
<221> NAME/KEY: site
<222> LOCATION: (1)..(1)
<223> OTHER INFORMATION: Modified Cys: N-carbamoyl and S-(EtOC(O)C15H31)

<400> SEQUENCE: 4

Cys Ser Lys Lys Lys Lys
1               5

<210> SEQ ID NO 5
<211> LENGTH: 18
<212> TYPE: PRT
<213> ORGANISM: Artificial Sequence
<220> FEATURE:
<223> OTHER INFORMATION: Synthetic protected MHC 1 epitope bound to
      solid phase
<220> FEATURE:
<221> NAME/KEY: site
<222> LOCATION: (1)..(1)
<223> OTHER INFORMATION: tert-butyl protected Asp
<220> FEATURE:
<221> NAME/KEY: site
<222> LOCATION: (2)..(2)
<223> OTHER INFORMATION: tert-butyl protected Glu
<220> FEATURE:
<221> NAME/KEY: site
<222> LOCATION: (4)..(4)
<223> OTHER INFORMATION: tert-butyl protected Ser
<220> FEATURE:
<221> NAME/KEY: site
<222> LOCATION: (7)..(7)
<223> OTHER INFORMATION: tert-butyl protected Glu
<220> FEATURE:
```

```
<221> NAME/KEY: site
<222> LOCATION: (8)..(8)
<223> OTHER INFORMATION: trityl protected Gln
<220> FEATURE:
<221> NAME/KEY: site
<222> LOCATION: (10)..(10)
<223> OTHER INFORMATION: tert-butyl protected Glu
<220> FEATURE:
<221> NAME/KEY: site
<222> LOCATION: (11)..(11)
<223> OTHER INFORMATION: trityl protected Ser
<220> FEATURE:
<221> NAME/KEY: site
<222> LOCATION: (14)..(14)
<223> OTHER INFORMATION: trityl protected Asn
<220> FEATURE:
<221> NAME/KEY: site
<222> LOCATION: (16)..(16)
<223> OTHER INFORMATION: tert-butyl protected Glu
<220> FEATURE:
<221> NAME/KEY: site
<222> LOCATION: (17)..(17)
<223> OTHER INFORMATION: Boc-protected Lys
<220> FEATURE:
<221> NAME/KEY: site
<222> LOCATION: (18)..(18)
<223> OTHER INFORMATION: solid-phase bound Leu

<400> SEQUENCE: 5

Asp Glu Val Ser Gly Leu Glu Gln Leu Glu Ser Ile Ile Asn Phe Glu
1               5                   10                  15

Lys Leu

<210> SEQ ID NO 6
<211> LENGTH: 18
<212> TYPE: PRT
<213> ORGANISM: Artificial Sequence
<220> FEATURE:
<223> OTHER INFORMATION: Synthetic protected MHC 1 epitope bound to
      solid phase
<220> FEATURE:
<221> NAME/KEY: site
<222> LOCATION: (1)..(1)
<223> OTHER INFORMATION: t-butyl protected Asp
<220> FEATURE:
<221> NAME/KEY: site
<222> LOCATION: (2)..(2)
<223> OTHER INFORMATION: t-butyl protected Glu
<220> FEATURE:
<221> NAME/KEY: site
<222> LOCATION: (4)..(4)
<223> OTHER INFORMATION: t-butyl protected Ser
<220> FEATURE:
<221> NAME/KEY: site
<222> LOCATION: (7)..(7)
<223> OTHER INFORMATION: t-butyl protected Glu
<220> FEATURE:
<221> NAME/KEY: site
<222> LOCATION: (8)..(8)
<223> OTHER INFORMATION: trityl protected Gln
<220> FEATURE:
<221> NAME/KEY: site
<222> LOCATION: (10)..(10)
<223> OTHER INFORMATION: t-butyl protected Glu
<220> FEATURE:
<221> NAME/KEY: site
<222> LOCATION: (11)..(11)
<223> OTHER INFORMATION: trityl protected Ser
<220> FEATURE:
<221> NAME/KEY: site
<222> LOCATION: (14)..(14)
<223> OTHER INFORMATION: trityl protected Asn
<220> FEATURE:
<221> NAME/KEY: site
<222> LOCATION: (16)..(16)
<223> OTHER INFORMATION: t-butyl protected Glu
```

```
<220> FEATURE:
<221> NAME/KEY: site
<222> LOCATION: (17)..(17)
<223> OTHER INFORMATION: azido-Lys
<220> FEATURE:
<221> NAME/KEY: site
<222> LOCATION: (18)..(18)
<223> OTHER INFORMATION: solid phase bound Leu

<400> SEQUENCE: 6

Asp Glu Val Ser Gly Leu Glu Gln Leu Glu Ser Ile Ile Asn Phe Glu
1               5                   10                  15

Lys Leu

<210> SEQ ID NO 7
<211> LENGTH: 18
<212> TYPE: PRT
<213> ORGANISM: Artificial Sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
<223> OTHER INFORMATION: Adjuvant conjugated to terminal Asp of MHC
      epitope

<400> SEQUENCE: 7

Asp Glu Val Ser Gly Leu Glu Gln Leu Glu Ser Ile Ile Asn Phe Glu
1               5                   10                  15

Lys Leu

<210> SEQ ID NO 8
<211> LENGTH: 18
<212> TYPE: PRT
<213> ORGANISM: Artificial Sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
<223> OTHER INFORMATION: Adjuvant conjugated to terminal Asp
<220> FEATURE:
<221> NAME/KEY: site
<222> LOCATION: (1)..(1)
<223> OTHER INFORMATION: Adjuvant conjugated to terminal Asp of MHC
      epitope
<220> FEATURE:
<221> NAME/KEY: misc_feature
<222> LOCATION: (17)..(17)
<223> OTHER INFORMATION: Xaa can be any naturally occurring amino acid

<400> SEQUENCE: 8

Asp Glu Val Ser Gly Leu Glu Gln Leu Glu Ser Ile Ile Asn Phe Glu
1               5                   10                  15

Xaa Leu

<210> SEQ ID NO 9
<211> LENGTH: 18
<212> TYPE: PRT
<213> ORGANISM: Artificial Sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
<223> OTHER INFORMATION: Adjuvant conjugated to terminal Asp
<220> FEATURE:
<221> NAME/KEY: site
<222> LOCATION: (1)..(1)
<223> OTHER INFORMATION: Adjuvant conjugated to terminal Asp of MHC
```

```
        epitope
<220> FEATURE:
<221> NAME/KEY: site
<222> LOCATION: (17)..(17)
<223> OTHER INFORMATION: Azido-modified Lys

<400> SEQUENCE: 9

Asp Glu Val Ser Gly Leu Glu Gln Leu Glu Ser Ile Ile Asn Phe Glu
1               5                   10                  15

Lys Leu

<210> SEQ ID NO 10
<211> LENGTH: 18
<212> TYPE: PRT
<213> ORGANISM: Artificial Sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
<223> OTHER INFORMATION: Adjuvant conjugated to terminal Asp
<220> FEATURE:
<221> NAME/KEY: site
<222> LOCATION: (1)..(1)
<223> OTHER INFORMATION: Adjuvant conjugated to terminal Asp of MHC
       epitope
<220> FEATURE:
<221> NAME/KEY: site
<222> LOCATION: (17)..(17)
<223> OTHER INFORMATION: Azido-modified Lys

<400> SEQUENCE: 10

Asp Glu Val Ser Gly Leu Glu Gln Leu Glu Ser Ile Ile Asn Phe Glu
1               5                   10                  15

Lys Leu

<210> SEQ ID NO 11
<211> LENGTH: 18
<212> TYPE: PRT
<213> ORGANISM: Artificial Sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
<223> OTHER INFORMATION: Adjuvant conjugated to terminal Asp
<220> FEATURE:
<221> NAME/KEY: site
<222> LOCATION: (1)..(1)
<223> OTHER INFORMATION: Adjuvant conjugated to terminal Asp of MHC
       epitope
<220> FEATURE:
<221> NAME/KEY: site
<222> LOCATION: (17)..(17)
<223> OTHER INFORMATION: Lys modified with linker to Cy5 dye

<400> SEQUENCE: 11

Asp Glu Val Ser Gly Leu Glu Gln Leu Glu Ser Ile Ile Asn Phe Glu
1               5                   10                  15

Lys Leu

<210> SEQ ID NO 12
<211> LENGTH: 18
<212> TYPE: PRT
<213> ORGANISM: Artificial sequence
<220> FEATURE:
<223> OTHER INFORMATION: Synthetic TLR-2 agonist-peptide conjugate
<220> FEATURE:
<221> NAME/KEY: site
<222> LOCATION: (1)..(1)
```

```
<223> OTHER INFORMATION: Adjuvant conjugated to terminal Asp
<220> FEATURE:
<221> NAME/KEY: site
<222> LOCATION: (1)..(1)
<223> OTHER INFORMATION: Adjuvant conjugated to terminal Asp of MHC
      epitope
<220> FEATURE:
<221> NAME/KEY: site
<222> LOCATION: (17)..(17)
<223> OTHER INFORMATION: Lys modified with linker to Cy5 dye

<400> SEQUENCE: 12

Asp Glu Val Ser Gly Leu Glu Gln Leu Glu Ser Ile Ile Asn Phe Glu
1               5                   10                  15

Lys Leu
```

PEPTIDE-CONTAINING ADJUVANT COMPOUNDS HAVING PEG SPACERS

FIELD OF THE INVENTION

The present invention relates to compounds active as adjuvants for modulating immune responses, their conjugation with antigenic peptides and other immunostimulatory agents and their uses in therapy.

BACKGROUND OF THE INVENTION

Vaccination has been used for decades to protect patients from developing a disease after contact with an infectious agent. To this end live attenuated, dead or disrupted pathogens, pathogen preparations, or purified or recombinant components of the pathogens have been administered to patients to elicit a specific immune response to antigenic components of the respective pathogen. The components, which stimulate such an immune response can be, for example, pathogen specific proteins, polysaccharides or lipids. The specific immune response against antigens comprised within pathogens can be further stimulated by the co-administration of adjuvants.

Adjuvants are known in the art to accelerate, prolong, or enhance the quality of the specific immune response to the antigen or antigens and are currently employed as part of vaccines. The advantages of adjuvants include their ability to: 1) direct and optimize immune responses that are appropriate for the vaccine; 2) enable mucosal delivery of vaccines; 3) promote cell-mediated immune response; 4) enhance the immunogenicity of weaker immunogens such as highly purified or recombinant antigens; 5) reduce the amount of antigen or the frequency of immunization required to provide protective immunity; 6) improve efficacy of vaccines in individuals with reduced or weakened immune responses such as newborns, the aged, and immunocompromised patients.

The human immune system consists of two interdependent parts, namely the adaptive and the innate system. As part of the innate immune system dendritic cells (DCs) express pattern recognition receptors (PRRs) that can bind non-self molecular structures termed pathogen associated molecular patterns (PAMPs). Upon binding of a PAMP to the corresponding PRR, signal transduction pathways are initiated that ultimately lead to adaptive immune responses.

The best known PRRs are the Toll-like receptors and in humans ten different versions of TLRs are detected, with lipopeptides derived from the outer membrane of *Escherichia coli* being well known agonists for the TLR-2. Several studies towards the optimization of TLR-2 ligands have been reported, including from the group of David et al., who developed mono- and bis-palmitoylated cysteines derivatives as potent TLR-2 ligands (Agnihotri, G. et al. Structure—Activity Relationships in Toll-Like Receptor 2-Agonists Leading to Simplified Monoacyl Lipopeptides. *J. Med. Chem.* 54, 8148-8160 (2011); Salunke, D. B. et al. Design and development of stable, water-soluble, human toll-like receptor 2 specific monoacyl lipopeptides as candidate vaccine adjuvants. *J. Med. Chem.* 56, 5885-5900 (2013); Salunke, D. B. et al. Structure-activity relationships in human toll-like receptor 2-specific monoacyl lipopeptides. *J. Med. Chem.* 55, 3353-3363 (2012)), while the synthetic $Pam_3CysSK_4$ lipopeptide, one of the most potent agonists for TLR-2, is used as an adjuvant in the development of new vaccines. For instance, conjugates of immunogenic peptides with $Pam_3CysSK_4$ resulted in highly potent self-adjuvanting vaccine conjugates (Khan, S. et al. Chirality of TLR-2 ligand Pam3CysSK4 in fully synthetic peptide conjugates critically influences the induction of specific CD8+ T-cells. *Mol. Immunol.* 46, 1084-1091 (2009); Zom, G. G. P., Khan, S., Filippov, D. V. & Ossendorp, F. *TLR Ligand-Peptide Conjugate Vaccines. Toward Clinical Application. Advances in Immunology* 114, (Elsevier Inc., 2012); Zom, G. G. et al. Two in one: improving synthetic long peptide vaccines by combining antigen and adjuvant in one molecule. *Oncoimmunology* 3, e947892 (2014); and Zom, G. G. et al. Efficient Induction of Antitumor Immunity by Synthetic Toll-like Receptor Ligand-Peptide Conjugates. *Cancer Immunol. Res.* 2, 756-764 (2014)).

However, the widening of the applicability of this class of conjugates is hindered by solubility issues. The lipophilicity of the $Pam_3Cys$ ligand in combination with the physical properties of antigenic peptides can result in unwanted aggregation or insolubility of the conjugates in mixtures of DMSO and/or aqueous buffers, by which the immunological effects and the evaluation thereof can be hampered.

There therefore remains a need for adjuvant compounds capable of eliciting enhanced immune responses while having better bioavailability.

The present invention is based in part on the surprising finding that a new class of TLR-2 ligand is able enhance an immune response relative to known ligands, while also having better bioavailability.

SUMMARY OF THE INVENTION

According to a first aspect of the invention, there is provided a compound of Formula (I):

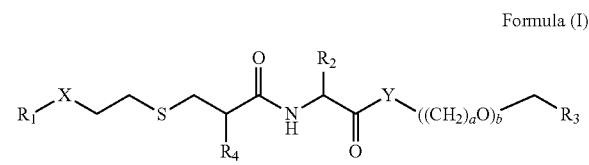

Formula (I)

or a pharmaceutically acceptable salt, solvate or prodrug thereof, wherein:
X is selected from —C(O)—O—, —O—C(O)—, —C(O)—, —C(O)—NH—, —NH—C(O)—, —NH—C(O)—O— and —O—C(O)—NH—;
Y is selected from —O—, —S— and —NH—;
a is 2 or 3;
b is 1, 2, 3, 4, 5 or 6;
$R_1$ is selected from a $C_{14-17}$ alkyl group;
$R_2$ is selected from H and $C_{1-6}$ alkyl, which is unsubstituted or substituted with a functional group selected from the group consisting of —OH, —OR', —$NH_2$, —NHR', —NR'$_2$, —SH, —SR', —O—C(O)R', —C(O)R', an amino acid or side chain thereof, and R' is selected from radicals consisting of H, $C_{1-10}$ alkyl, $C_{2-10}$ alkenyl, $C_{2-10}$ alkynyl, aryl, heteroaryl, an amino acid or side chain thereof, and $SO_2H$;
$R_3$ is selected from —C(O)—$R_5$, —C(O)—$OR_6$, and —C(O)—$NHR_6$, in which
$R_5$ is selected from $NH_2$, an amino acid side chain, one or more nucleic acids, one or more antibodies or fragments thereof, one or more carbohydrates or fragments thereof, one or more peptides or fragments thereof, H, and $C_{1-20}$ alkyl, which is unsubstituted or optionally substituted with a functional group selected from the group consisting of —OH, —OR', —NH₂, —NHR', —NR'₂, —SH, —SR', —O—C(O)R', —C(O)R', —CF₃, —OCF₃, an amino acid side chain, one or more nucleic acids, one or more antibodies or fragments thereof, one or more carbohydrates or fragments thereof, one or more peptides or fragments thereof, and R' is selected from radicals consisting of H, $C_{1-10}$ alkyl, $C_{2-10}$ alkenyl and $C_{2-10}$ alkynyl, an amino acid side chain, one or more nucleic acids, one or more antibodies or fragments thereof, one or more carbohydrates or fragments thereof, one or more peptides or fragments thereof;

$R_6$ is from an amino acid side chain, one or more nucleic acids, one or more antibodies or fragments thereof, one or more carbohydrates or fragments thereof, one or more peptides or fragments thereof, H, and $C_{1-20}$ alkyl, which is unsubstituted or optionally substituted with a functional group selected from the group consisting of —OH, —OR', —NH₂, —NHR', —NR'₂, —SH, —SR', —O—C(O)R', —C(O)R', —CF₃, —OCF₃, an amino acid side chain, one or more nucleotides, one or more antibodies or fragments thereof, one or more carbohydrates or fragments thereof, one or more peptides or fragments thereof, and R' is selected from radicals consisting of H, $C_{1-10}$ alkyl, $C_{2-10}$ alkenyl and $C_{2-10}$ alkynyl, an amino acid side chain, one or more nucleic acids, one or more antibodies or fragments thereof, one or more carbohydrates or fragments thereof, one or more peptides or fragments thereof; and $R_4$ is selected from —NH₂, and —NH—C(O)—R₇, in which $R_7$ is selected from NH₂, an amino acid side chain, H, and $C_{1-20}$ alkyl, which is unsubstituted or optionally substituted with a functional group selected from the group consisting of —OH, —OR', —NH₂, —NHR', —NR'₂, —SH, —SR', —O—C(O)R', —C(O)R', —CF₃, —OCF₃, an amino acid side chain, and R' is selected from radicals consisting of H, $C_{1-10}$ alkyl, $C_{2-10}$ alkenyl and $C_{2-10}$ alkynyl.

The specific compounds of Formula (I) and preferred or exemplified sub-classes of compounds of Formula (I) as discussed below may be particularly mentioned for use in the present invention.

Particularly preferred compounds are those of Formula (I) in which variant X is selected from —C(O)—O— and —C(O)—NH—.

Particularly preferred compounds are those in which a is 2. Particularly preferred compounds are those in which b is 2, 3 or 4, particularly those compounds in which b is 3. Particularly preferred compounds are those in which a is 2 and b is 3.

Particularly preferred compounds are those in which $R_1$ is $C_{15}$ alkyl.

Particularly preferred compounds are those in which $R_2$ is $C_{1-6}$ hydroxyalkyl, for example hydroxymethyl.

Particularly preferred compounds are those in which $R_3$ is —C(O)—OR₆ or —C(O)—NHR₆ in which $R_5$ is selected from H and a peptide or a fragment thereof. The peptide may be a peptide antigen. The peptide fragment may be an antigenic fragment of the peptide.

Particularly preferred compounds are those in which $R_4$ is —NH—C(O)—R₇, in which $R_7$ is selected from H, NH₂, $C_{1-6}$ alkyl, and an amino acid side chain.

In one example, $R_4$ is —NH—C(O)—R₇, in which $R_7$ comprises an amino acid side chain, such as a charged amino acid side chain as may be found on arginine, lysine, aspartic acid and glutamic acid; a polar amino acid side chain as may be found on glutamine, asparagine, histidine, serine, threonine, tyrosine, cysteine, methionine and tryptophan; or a hydrophobic amino acid side chain such as may be found on alanine, isoleucine, leucine, phenylalanine, valine, proline and glycine.

Particularly preferred compounds are those in which: X is selected from —C(O)—O— and —C(O)—NH—; a is 2 and b is 3; $R_1$ is $C_{15}$ alkyl; $R_2$ is $C_{1-6}$ hydroxyalkyl; $R_3$ is —C(O)—OR₆, or —C(O)—NHR₆ in which $R_6$ is selected from H, a nucleic acid, a carbohydrate, an antibody or a fragment thereof and a peptide or a fragment thereof; and $R_4$ is —NH—C(O)—R₇, in which $R_7$ is NH₂.

Particularly preferred compounds include those shown as compounds 6 and 7 in FIG. 1 of the present disclosure:

(14S,17S)-14-(hydroxymethyl)-13,16,24-trioxo-17-ureido-3,6,9,12,23-pentaoxa-20-thia-15-azanonatriacontanoic acid (6) and (14S,17 S)-14-(hydroxymethyl)-13,16,24-trioxo-17-ureido-3,6,9,23-tetraoxa-20-thia-12,15-diazanonatriacontanoic acid (7).

According to a second aspect of the present invention there is provided a conjugate comprising a peptide or a fragment thereof covalently bonded to a compound of Formula (I):

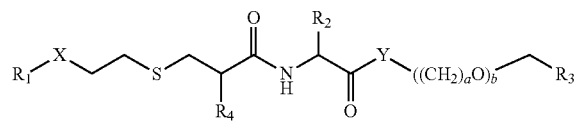

Formula (I)

or a pharmaceutically acceptable salt, solvate or prodrug thereof, wherein:

X is selected from —C(O)—O—, —O—C(O)—, —C(O)—, —C(O)—NH—, —NH—C(O)—, —NH—C(O)—O— and —O—C(O)—NH—;

Y is selected from —O—, —S— and —NH—;

a is 2 or 3;

b is 1, 2, 3, 4, 5 or 6;

$R_1$ is selected from a $C_{14-17}$ alkyl group;

$R_2$ is selected from H and $C_{1-6}$ alkyl, which is unsubstituted or substituted with a functional group selected from the group consisting of —OH, —OR', —NH₂, —NHR', —NR'₂, —SH, —SR', —O—C(O)R', —C(O)R', an amino acid or side chain thereof, and R' is selected from H, $C_{1-10}$ alkyl, $C_{2-10}$ alkenyl, $C_{2-10}$ alkynyl, aryl, heteroaryl, an amino acid or side chain thereof, and SO₂H;

$R_3$ is selected from —C(O)—R₅, —C(O)—OR₆, and —C(O)—NHR₆; in which $R_5$ is selected from a peptide or a fragment thereof, and $C_{1-20}$ alkyl substituted with a functional group selected from the group consisting of —OR', —NHR', —NR'₂, —SR', —O—C(O)R', —C(O)R', a peptide or a fragment thereof, and R' is selected from radicals consisting of $C_{1-10}$ alkyl, $C_{2-10}$ alkenyl and $C_{2-10}$ alkynyl substituted with a peptide or a fragment thereof; or $R_6$ is selected from a peptide or a fragment thereof, and $C_{1-20}$ alkyl substituted with a functional group selected from the group consisting of —OR', —NHR', —NR'₂, —SR', —O—C(O)R', —C(O)R', a peptide or a fragment thereof, and R' is selected from radicals consisting of H, $C_{1-10}$ alkyl, $C_{2-10}$ alkenyl and $C_{2-10}$ alkynyl substituted with a peptide or a fragment thereof; and $R_4$ is selected from —$NH_2$, and —NH—C(O)—$R_7$, in which $R_7$ is selected from $NH_2$, an amino acid side chain, H, and $C_{1-20}$ alkyl, which is unsubstituted or optionally substituted with a functional group selected from the group consisting of —OH, —OR', —$NH_2$, —NHR', —NR'$_2$, —SH, —SR', —O—C(O)R', —C(O)R', —$CF_3$, —$OCF_3$, an amino acid side chain, and R' is selected from radicals consisting of H, $C_{1-10}$ alkyl, $C_{2-10}$ alkenyl, and $C_{2-10}$ alkynyl.

Particularly preferred conjugates are those in which $R_2$ is $C_{1-6}$ hydroxyalkyl, for example hydroxymethyl.

Particularly preferred conjugates are those in which $R_3$ is selected from —C(O)—$OR_6$ or —C(O)—$NHR_6$, in which $R_6$ comprises the peptide or a fragment thereof.

Particularly preferred conjugates are those in which $R_4$ is —NH—C(O)—$R_7$, in which $R_7$ is selected from H, $NH_2$, $C_{1-6}$ alkyl, and an amino acid side chain.

Particularly preferred conjugates are those in which X is selected from —C(O)—O— and —C(O)—NH—.

Particularly preferred conjugates are those in which a is 2. Particularly preferred conjugates are those in which b is 2, 3 or 4, particularly those conjugates in which b is 3. Particularly preferred conjugates are those in which a is 2 and b is 3.

Particularly preferred conjugates are those in which $R_1$ is $C_{15}$ alkyl.

Particularly preferred conjugates are those in which the peptide comprises a peptide vaccine or antigen.

Particularly preferred conjugates are those in which the peptide fragment comprises an antigenic fragment of the peptide.

Particularly preferred compounds are those in which: X is selected from —C(O)—O— and —C(O)—NH—; a is 2 and b is 3; $R_1$ is $C_{15}$ alkyl; $R_2$ is $C_{1-6}$ hydroxyalkyl; $R_3$ is —C(O)—$OR_6$, in which $R_6$ comprises a peptide or a fragment thereof; and $R_4$ is —NH—C(O)—$R_7$, in which $R_7$ is $NH_2$.

Particularly preferred conjugates are those in which compounds 6 or 7 of FIG. 1 are conjugated via the free carboxyl group to a peptide or fragment thereof.

According to a third aspect of the present invention there is provided a method of modulating an immune response in a subject in need thereof, comprising administering an effective amount of a compound of the first aspect or the conjugate of the second aspect to the subject.

According to a fourth aspect of the present invention there is provided a compound of the first aspect or a conjugate of the second aspect for use in a method of modulating an immune response in a subject in need thereof, the method comprising administering an effective amount of the compound of the first aspect or the conjugate of the second aspect to the subject.

According to a fifth aspect of the present invention there is provided the use of a compound of the first aspect as an adjuvant in therapy.

According to a sixth aspect of the present invention there is provided the use of a compound of the first aspect or the use of a conjugate of the second aspect in the preparation of a medicament for modulating an immune response in a subject in need thereof.

In any of the third to sixth aspects, a compound of the first aspect or a conjugate of the second aspect may be used to induce or enhance an immune response in a subject in need thereof.

The subject may have or may be susceptible to cancer, an infectious disease, a non-autoimmune metabolic or degenerative disease or an atopic disease.

Thus, the present invention also provides (i) a method of treating or preventing cancer; (ii) a method of treating or preventing a viral infection; (iii) a method of treating or preventing a bacterial infection; (iv) a method of treating or preventing a non-autoimmune metabolic disease; and (v) a method of treating or preventing an atopic disease, comprising administering an effective amount of the compound of the first aspect or the conjugate of the second aspect to a subject in need thereof.

Thus, the present invention also provides a compound or a conjugate as described herein for use in a (i) a method of treating or preventing cancer; (ii) a method of treating or preventing a viral infection; (iii) a method of treating or preventing a bacterial infection; (iv) a method of treating or preventing a non-autoimmune metabolic disease; and (v) a method of treating or preventing an atopic disease, the method comprising administering an effective amount of a compound of the first aspect or a conjugate of the second aspect to a subject in need thereof.

According to a seventh aspect of the present invention there is provided a kit-of-parts, comprising:
    a compound of the first aspect or a conjugate of the second aspect; and
    a therapeutic agent selected from a chemotherapeutic agent, an anti-inflammatory agent, an anti-viral agent.

According to an eighth aspect of the present invention there is provided a pharmaceutical composition comprising a compound of the first aspect or a conjugate of the second aspect in combination with or admixed with a pharmaceutical carrier and optionally one or more excipients.

BRIEF DESCRIPTION OF THE DRAWINGS

Embodiments of the present invention will now be described, purely by way of example, and with reference to the accompanying drawings, in which.

DETAILED DESCRIPTION OF THE INVENTION

Figure 1:
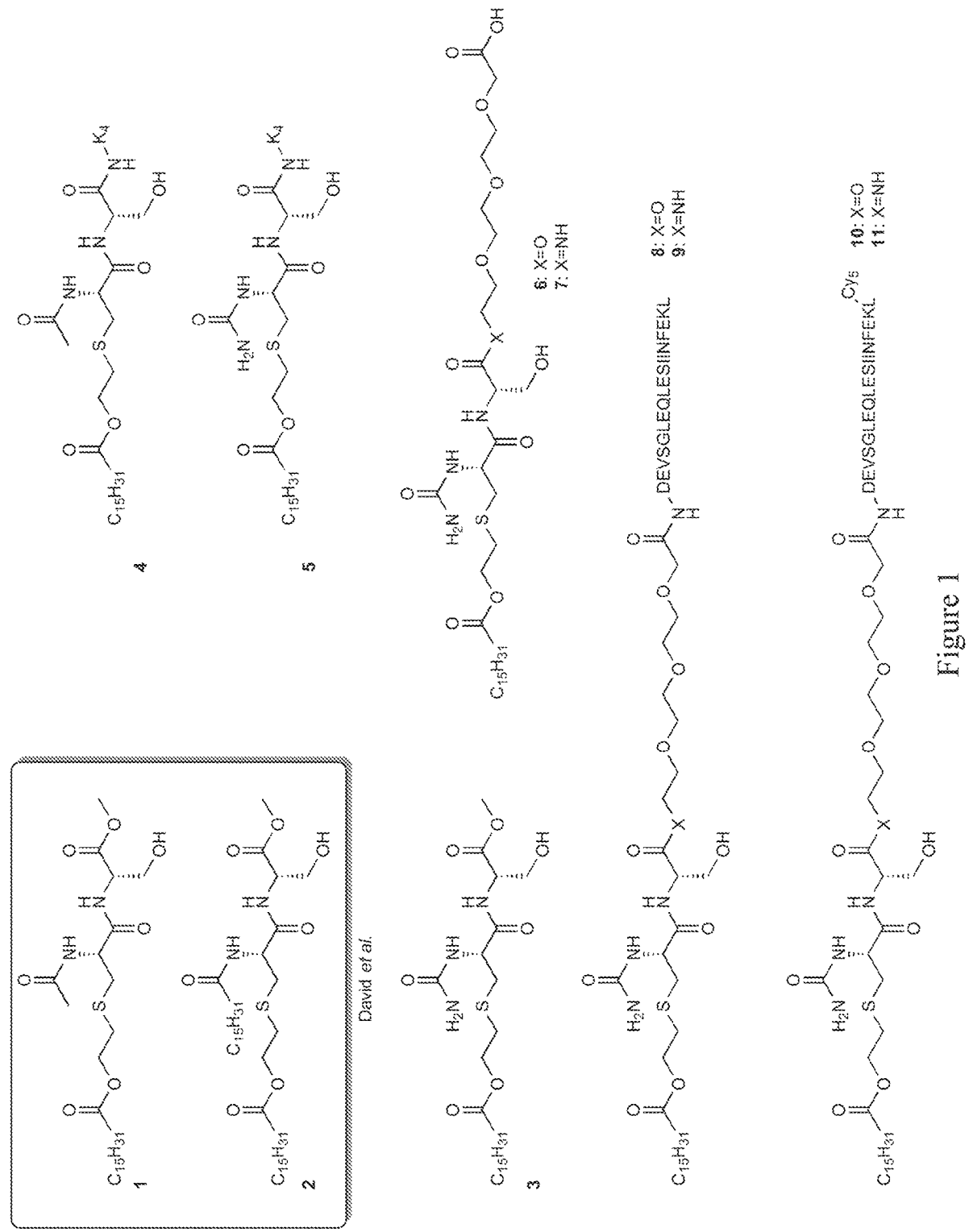
FIG. 1 shows the structures of selected self-adjuvanting TLR-2 lipopeptides.

The compounds of the present invention are TLR2-specific agonists and may therefore be used in methods of treating or preventing any disease, disorder or condition to which an immune response is required.

Definitions

In the definition of Formula (I) herein:

"$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group;

"$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group;

"$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group;

"$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group;

"$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group; "halogen atom" refers to a fluorine atom, a chlorine atom, a bromine atom, or an iodine atom;

"$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group;

"$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group;

"$C_{6-10}$ cycloalkyl" refers to a non-aromatic cyclic hydrocarbon group comprising 6 to 10 carbon atoms. Specifically, the "$C_{6-10}$ cycloalkyl" group includes, for example, a cyclohexyl group, and a decalin group.

"$C_{6-10}$ aryl group" refers to an aromatic cyclic hydrocarbon group comprising six to ten carbon atoms. Specifically, the $C_{6-10}$ aryl group includes, for example, a phenyl group, a 1-naphthyl group, and a 2-naphthyl group;

"$C_{5-10}$ heteroaryl group" refers to a heteroaromatic cyclic hydrocarbon group comprising a delocalized electronic structure wherein at least one, for example one or two, of the atoms constituting the ring are heteroatoms. Specifically, the $C_{5-10}$ heteroaryl group includes, for example, a furan ring, a pyrrole ring, an imidazole ring, a triazole ring, a diazole ring, a pyran ring, a pyridine ring, a pyridazine ring, a pyrimidine ring, and a pyrazine ring;

"heteroatom" refers to a sulfur atom, an oxygen atom, or a nitrogen atom.

As used herein, the phrase "may have one or more substituent" means that a certain group or compound is in the first instance unsubstituted but that it may optionally have an arbitrary selection or combination of one or more substituent at substitutable positions. Specifically, the substituents can include, for example, atoms or groups selected from one or more of: halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ alkoxy (for example, methoxy), $C_{1-6}$ alkylthio (for example methylthio), $C_{2-6}$ alkenyl, $C_{2-6}$ alkynyl; $C_{1-6}$ alkoxycarbonyl, $C_{1-6}$ alkylsulfonyl, $C_{6-10}$ cycloalkyl, $C_{6-10}$ aryl, benzyl, $C_{5-10}$ heteroaryl (for example pyridyl), phenyl, or $C_{6-10}$ cycloalkyl, $C_{6-10}$ aryl or benzyl or phenyl or $C_{5-10}$ heteroaryl (for example pyridyl) substituted by one or more of halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, or $C_{1-6}$ alkoxy (for example, methoxy) or as otherwise stated.

As used herein, reference to an element by the indefinite article "a" or "an" does not exclude the possibility that more than one of the elements is present, unless the context clearly requires that there be one and only one of the elements. The indefinite article "a" or "an" thus usually means "at least one".

As used herein, the verb "to comprise" and its conjugations is used in its non-limiting sense to mean that items following the word are included, but items not specifically mentioned are not excluded. In addition the verb "to consist" may be replaced by "to consist essentially of" meaning that a compound or a composition as defined herein may comprise additional component(s) than the ones specifically identified, said additional component(s) not altering the unique characteristic of the invention.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the terms "optional" or "optionally" mean that the subsequently described circumstance may or may not occur, such that the description includes instances where the circumstance occurs and instances where it does not.

As used herein, the term "modulate," means that any of the mentioned activities of the compounds embodied herein, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

As used herein, "agonist" generally refers to a compound, for example an exogenous compound that binds to a receptor and mimics the effects of an endogenous compound. Further, the term "agonist" refers to both full and/or partial agonists. A full agonist shows full efficacy at a receptor, while a partial agonist shows only partial efficacy at a receptor relative to a full agonist. Unless otherwise indicated, reference to a TLR-2 agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

Regardless of the particular assay employed, a compound can be identified as an agonist of TLR-2 if performing the assay with a compound results in at least a threshold modulation, e.g. increase, of some biological activity mediated by TLR-2. Conversely, a compound may be identified as not acting as an agonist of TLR-2 if, when used to perform an assay designed to detect biological activity mediated by TLR-2, the compound fails to elicit a threshold modulation, e.g. increase, in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR-2 agonism of a compound in a particular assay.

The precise threshold increase of TLR-2-mediated biological activity for determining whether a particular compound is or is not an agonist of TLR-2 in a given assay may vary according to factors known in the art including but not limited to the biological activity observed as the endpoint of the assay, the method used to measure or detect the endpoint of the assay, the signal-to-noise ratio of the assay, the precision of the assay, and whether the same assay is being used to determine the agonism of a compound for multiple TLRs. Accordingly it is not practical to set forth generally the threshold increase of TLR-mediated biological activity required to identify a compound as being an agonist or a non-agonist of a particular TLR for all possible assays. Those of ordinary skill in the art, however, can readily determine the appropriate threshold with due consideration of such factors.

As used herein, the terms "compound" and "compounds" refer to a compound encompassed by Formula (I) herein, any subgenus of that generic formula, and any forms of the compounds within the generic formula. Unless specified otherwise, the term further includes the racemates and stereoisomers, of the compound or compounds. Certain compounds of the invention possess chiral centers and/or double bonds, and/or may have tautomers or atropisomers; the tautomeric, enantiomeric, diastereomeric, atropisomeric, and geometric mixtures of two or more isomers, in any composition, as well as the individual isomers (including tautomers and atropisomers) are encompassed within the scope of the present invention. Whenever the term "isomer" is used, it refers to an atropisomeric, tautomeric, enantiomeric, diastereomeric, and/or geometric isomer or to a mixture of two or more of these isomers, unless the context dictates otherwise.

As used herein, the term "amino acid" includes natural or unnatural amino acids, derivatives, isomers, homologs and the like. "Peptide fragments" as used herein, thus include, one or more "amino acids" as defined herein and peptidomimetics. The term "unnatural amino acid" is intended to represent the D stereoisomer of a naturally occurring amino acid.

Encompassed within this term include β-amino acids, derivatives, homologues and any non-naturally occurring amino acid known to those of skill in the art. The term "β-amino acid" refers to those amino acids in which their amino group is bonded to the β-carbon as opposed to the α-carbon represented by the standard biological amino acids. Representative amino acids include, but are not limited to, glycine, alanine, serine, threonine, arginine, lysine, ornithine, aspartic acid, glutamic acid, asparagine, glutamine, phenylalanine, tyrosine, tryptophan, leucine, valine, isoleucine, cysteine, methionine, histidine, 4-trifluoromethyl-phenylalanine, 3-(2-pyridyl)-alanine, 3-(2-furyl)-alanine, 2,4-diaminobutyric acid, and the like. Peptides or amino acid side chains include, without limitation: α-amino acids, β-amino acids and hybrid oligopeptides comprising α- and β-amino acids.

A "derivative" amino acid or peptide is one that is modified, for example, by glycosylation, pegylation, phosphorylation, sulfation, reduction alkylation, acylation, chemical coupling, or mild formalin treatment. A derivative may also be modified to contain a detectable label, either directly or indirectly, including, but not limited to, a radio-isotope, fluorescent, and enzyme label. A "derivative compound" includes, without limitation, peptide molecules in which free amino groups have been derivatized to form salts or amides, by adding acetyl groups, amine hydrochlorides, carbobenzoxy groups, chloroacetyl groups, formyl groups, p-toluene sulfonyl groups, or t-butyloxycarbonyl groups. Free hydroxyl groups may be derivatized to form O-acyl or O-alkyl derivatives. Furthermore, free carboxyl groups may be derivatized to form salts, esters (e.g., methyl and ethyl esters), or hydrazides. Thus, a "derivative" further includes any pharmaceutically-acceptable salt of a derivative as described herein.

The term "chiral" is used to describe an object that is nonsuperposable on its mirror image and therefore has the property of chirality.

The term "chirality" refers to the geometric property of a rigid object (or spatial arrangement of points or atoms) of being non-superposable on its mirror image. If the object is superposable on its mirror image the object is described as being achiral.

The term "chirality axis" refers to an axis about which a set of ligands is held so that it results in a spatial arrangement which is not superposable on its mirror image.

The term "chirality center" refers to an atom holding a set of ligands in a spatial arrangement, which is not superposable on its mirror image. A chirality center may be considered a generalized extension of the concept of the asymmetric carbon atom to central atoms of any element. Each chiral center is labeled R or S according to a system by which its substituents are each designated a priority according to the Cahn Ingold Prelog priority rules (CIP), based on atomic number. According to some embodiments, the stereochemistry of the chiral centers represents all possible combinations in terms of relative and absolute chemistry. Accordingly, it may represent either racemates or pure enantiomers.

The term "racemate" as used herein refers to an equimolar mixture of two optically active components that neutralize the optical effect of each other and is therefore optically inactive.

The term "enantiomer" refers to one of a pair of optical isomers containing one or more asymmetric carbons whose molecular configurations have left- and right-hand (chiral) forms. Enantiomers have identical physical properties, except for the direction of rotation of the plane of polarized light. Enantiomers have identical chemical properties except toward optically active reagents.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). "Stereoisomer" or "stereoisomers" refer to compounds that differ in the chirality of one or more stereocenters. Stereoisomers may include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

As used herein, the term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

As used herein, the term "carbohydrate" refers to one or more monosaccharides, and encompasses within its definition disaccharides, oligosaccharides and polysaccharides or glycans. The term "carbohydrate" therefore encompasses the carbohydrate portion of a glycoconjugate, such as a glycoprotein, glycolipid or proteoglycan. The carbohydrate may be a straight chain carbohydrate or a branched chain carbohydrate.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds, conjugates or their derivatives.

Compounds and Conjugates

Compounds of the present invention are as defined by Formula (I) and have been shown to be agonists of the TLR-2 receptor, and thus are useful in treatments of diseases as described herein in which an enhanced immune response may be beneficial.

The compounds of the present invention may be synthesised by any known method. An exemplary synthesis is described below in the Examples.

The present invention thus also provides a method of preparing a compound or conjugate of Formula (I), comprising:

providing a compound of Formula (I) in which $R_3$ is —$CO_2H$;

activating the —$CO_2H$ at the $R_3$ position to generate an active ester of the compound of Formula (I); and coupling the active ester of the compound of Formula (I) with a primary or secondary amine present on one or more nucleic acids, one or more antibodies or fragments thereof, one or more carbohydrates or fragments thereof, one or more peptides or fragments thereof as described herein.

Activating the —$CO_2H$ at the $R_3$ position to generate an active ester may be achieved using any reagent used for such purposes in peptide coupling reactions. Suitable activating agents include HATU, HBTU, HCTU, TBTU, PyBOP, DIC, DCC, HOBt, and HOAt, as will be known in the person skilled in the art.

In the example in which a compound of Formula (I) is coupled with a peptide or fragment thereof, the coupling may take place via the N-terminal amino group. In one example, the one or more nucleic acids, one or more antibodies or fragments thereof, one or more carbohydrates or fragments thereof, one or more peptides or fragments thereof may be bound to a solid surface prior to the coupling reaction. In another example, the one or more nucleic acids, one or more antibodies or fragments thereof, one or more carbohydrates or fragments thereof, one or more peptides or fragments thereof may be in the solution phase.

The compounds of the present invention contain at least two stereocentres, namely the carbon atoms to which the $R_2$ and $R_4$ groups are bonded. While the present invention encompasses the racemic mixture of the compounds, in one example it is preferred for the compounds (or conjugates) to have the configuration at the two stereocentres as shown in FIG. 1.

In one example, $R_3$ of a compound of Formula (I) is selected from —C(O)—$R_5$, —C(O)—$OR_6$, and —C(O)—$NHR_6$, in which $R_5$ or $R_6$ is H. The compounds of this example may be used in a combination therapy with, for example, one or more nucleic acids, one or more antibodies or fragments thereof, one or more carbohydrates or fragments thereof, one or more peptides or fragments thereof as described herein. The combination therapy may be used in the treatment or prevention of any disease as described herein. The combination therapy may comprise prior, concomitant or subsequent co-administration of the compound to a subject in need thereof relative to an antigen as is described herein, or another chemotherapeutic, anti-viral, anti-bacterial or other pharmaceutically active compound.

However, through the $R_3$ position, the compounds of Formula (I) can also be conjugated to one or more nucleic acids, one or more antibodies or fragments thereof, one or more carbohydrates or fragments thereof, one or more peptides or fragments thereof to form conjugate molecules for use in therapy.

In one example, $R_3$ of a compound of Formula (I) is selected from —C(O)—$R_5$, —C(O)—$OR_6$, and —C(O)—$NHR_6$, in which $R_5$ or $R_6$ comprises an organic group comprising one or more nucleic acids, such as one or more oligonucleotides or one or more polynucleotides, preferably one or more oligonucleotides. An oligonucleotide may be a sense or an antisense oligonucleotide. In this respect, the compound according to the invention is referred to as an adjuvant-nucleic acid conjugate. In one example, the nucleic acid is an antigen.

In the context of this invention, a "nucleic acid" preferably has a length of 5 to 60 nucleotides (i.e. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides). A nucleic acid such as a polynucleotide and an oligonucleotide may be any nucleic acid known to the person skilled in the art, such as a DNA, RNA, PNA or combinations thereof. Thus, a nucleic acid may comprise naturally occurring nucleotides, or nucleotides analogues, which have one or more modifications with respect to naturally occurring nucleotides. In this respect, naturally occurring nucleotides are those which are comprised in DNA or RNA. Nucleotides analogues comprise at least one modification selected from a modified nucleobase, a modified sugar moiety, a modified internucleoside linkage, and combinations thereof. One example of such modifications is a modified backbone, comprising a modified sugar moiety and/or a modified internucleoside linkage. Thus, the backbone and nucleobases of the nucleic acid may be modified according to techniques commonly known to the person skilled in the art, in order to enhance or reduce specificity and/or to enhance or decrease stability. Accordingly, a nucleic acid may contain a RNA residue, a DNA residue, a nucleotide analogue or equivalent as will be further detailed herein below.

It is preferred that a nucleic acid comprises at least one residue that is modified to increase nuclease resistance, and/or to increase the affinity of an (antisense) nucleotide for a target sequence. Therefore, in a preferred embodiment, a nucleic acid comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, a nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500).

PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer. Since the backbone of a PNA molecule contains no charged phosphate groups, PNA-RNA hybrids are usually more stable than RNA-RNA or RNA-DNA hybrids, respectively.

In yet a further embodiment, a nucleotide analogue or equivalent of the invention comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower $C_{1-10}$alkyl, $C_{2-10}$alkenyl, $C_{2-10}$alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. These substitutions render the nucleotide analogue or equivalent RNase H and nuclease resistant and increase the affinity for the target RNA.

It is understood by a skilled person that it is not necessary for all positions in an (antisense) oligonucleotide to be modified uniformly. In addition, more than one of the aforementioned analogues or equivalents may be incorporated in a single (antisense) oligonucleotide or even at a single position within an (antisense) oligonucleotide. In certain embodiments, an (antisense) oligonucleotide of the invention has at least two different types of analogues or equivalents. In a preferred embodiment, the modification occurs over the full length of the oligonucleotide.

A preferred oligonucleotide is an immunomodulating oligonucleotide that may occur naturally or be a synthetic oligonucleotide. Preferably, such oligonucleotide immunomodulates by acting on a Toll-like receptor, preferably Toll-like receptor 9 (TLR9). Preferably, such oligonucleotide comprises one or more, such as 1, 2, 3, 4, 5, 6, 7 or more, CpG (unmethylated cytidine-phosphate-guanosine (CpG) dinucleotides), more preferably one or more, class B CpG. Class B CpG comprising oligonucleotides are strong stimulators of human B cell and monocyte maturation. A preferred class B CpG oligonucleotide comprises one or more, preferably three, of the 6mer CpG motif 5'-Pu Py C G Py Pu-3', a partly or fully phosphorothioated backbone, and is preferably 18 to 28 nucleotides, such as 18, 19, 20, 21, 22, 23, 24, 25, 26, 27 or 28 nucleotides, in length. Another preferred CpG comprising oligonucleotide comprises one or more, such as 1, 2, 3, 4, 5, 6, 7 or more, class A CpG. Class A CpG stimulate the production of large amounts of Type I interferons, especially IFNα, induce the maturation of pDCs, and/or are strong activators of NK cells through indirect cytokine signaling.

A preferred class A CpG oligonucleotide comprises one or more of a poly G sequence at the 5' end, the 3' end, or both, an internal palindrome sequence, one or more GC dinucleotides within the internal palindrome, and a partially phosphorothioated backbone, preferably 7 to 10 phosphorothioated bases at one or both ends.

The preparation of peptide/nucleic acid-conjugates is well-known in the art, for example from Carter and LeBean, *J. Nucleic Acids*, 2011 (doi:10.4061/2011/926595), which is incorporated by reference in its entirety.

In another example, $R_3$ of a compound of Formula (I) is selected from —C(O)—$R_5$, —C(O)—O$R_6$, and —C(O)—NH$R_6$, in which $R_5$ or $R_6$ comprises an organic group comprising one or more antibodies. In this respect, the compound according to the invention is referred to as an adjuvant-antibody conjugate. The antibody may be any antibody known to the person skilled in the art. Preferred antibodies are selected from the list consisting of 1) antibodies directed against specific target molecules on the surface of cancer cells: differentiation antigens such as CD19, CD20, CD30, overexpressed antigens such as HER-2/Neu, epidermal growth factor receptor (EGFR); 2) antibodies directed against surface molecules of T cells such as IL-2 receptor, IL-7 receptor, IL-15 receptor with the aim to delete a subset of T cells causing autoimmune disease or involved in immunoregulation such as non-activated regulatory T cells.

In another example, $R_3$ of a compound of Formula (I) is selected from —C(O)—$R_5$, —C(O)—O$R_6$, and —C(O)—NH$R_6$, in which $R_5$ or $R_6$ comprises an organic group comprising one or more carbohydrates. The carbohydrate may be an oligosaccharide or a polysaccharide or the glycan part of a glycoconjugate such as a glycoprotein, glycolipid or a proteoglycan. In this respect, the compound according to the invention is referred to as a carbohydrate-adjuvant conjugate. Many glycans on cancer cells differ from those of normal cells by, for example, truncation or even emergence of new glycans. In addition, carbohydrate structures on the cell surface of viral or bacterial pathogens are important antigens that can activate B cells to produce anti-carbohydrate antibodies in a subject. These carbohydrate structures are thus attractive targets for immunotherapy, for example, cancer immunotherapy, though by themselves are weakly immunogenic and so would benefit from conjugation with a compound of Formula (I). Non-limiting examples of carbohydrates or glycans which may be comprised within the definitions of $R_5$ and $R_6$ include Globo H, a hexasaccharide glycan found on a variety of cancer cells, as well as stage-specific embryonic antigen 3 (SSEA3; also called Gb5) which has been observed on breast cancer cells.

In another example, $R_3$ of a compound of Formula (I) is selected from —C(O)—$R_5$, —C(O)—O$R_6$, and —C(O)—NH$R_6$, in which $R_5$ or $R_6$ comprises an organic group comprising one or more peptides, or fragments thereof, such as one or more oligopeptides or one or more polypeptides. In this respect, the compound according to the invention is referred to as an adjuvant-peptide conjugate. In one example, the peptide is an antigen and the compounds is referred to as an adjuvant-antigen conjugate.

A preferred peptide antigen comprises a peptide comprising a T cell epitope, i.e. CD4 and/or CD8 T cell epitopes that are derived from any of the viral, non-viral, tumor, bacterial or parasite antigens described herein.

In some examples, the peptide antigen is derived from a viral antigen, for example from the high risk human papilloma virus (HPV)-specific E6 and E7 oncoproteins as described in WO02/070006 and WO2008/147187, which publications are hereby incorporated by reference.

In some examples, the peptide or antigenic fragment thereof may be derived from a non-viral tumor antigen.

For example, one peptide antigen for conjugation with a compound as described herein comprises a peptide comprising a CD4 and/or CD8 T cell epitope that is derived from the non-viral tumor antigen p53 as described in WO2008/147186, which publication is hereby incorporated by reference.

Another example of a peptide antigen comprises a peptide comprising CD4 and/or CD8 T cell epitopes that are derived from the non-viral tumor antigen PRAME as described in WO2008/118017, which publication is hereby incorporated by reference.

A further example of a peptide antigen comprises peptides comprising CD4 and/or CD8 T cell epitopes that are derived from the non-viral tumor antigen NY-ESO-1 as described in WO98/14464, which publication is hereby incorporated by reference.

A further example of a peptide antigen comprises peptides comprising CD4 and/or CD8 T cell epitopes that are derived from the non-viral tumor antigen XAGE-1B as described in U.S. Pat. Nos. 6,504,010 and 7,425,607, which publications are hereby incorporated by reference.

A further example of a peptide antigen comprises a peptide comprising CD4 and/or CD8 T cell epitopes that are derived from the non-viral tumor antigens such as PSA and PSMA as described in WO00/06723, which publication is hereby incorporated by reference.

A further example of a peptide antigen comprises peptides comprising CD4 and/or CD8 T cell epitopes that are derived from the bacterial antigens derived from *Mycobacterium tuberculosis* as described in WO06/104389, which publication is hereby incorporated by reference.

In another example, $R_3$ of a compound of Formula (I) is selected from —C(O)—$R_5$, —C(O)—$OR_6$, and —C(O)—$NHR_6$, in which $R_5$ or $R_6$ comprises an organic group comprising one or more peptides, or fragments thereof, wherein the peptide or an antigenic fragment thereof is derived from a subject's tumour mutanome.

The development of personalised or precision medicine based on a subject's own genetic make-up is of great importance in developing effective therapies. While there are an abundance of known mutations that lead to oncogenesis, only a handful of these are common across patient populations with the majority of mutations in a patient's tumour being unique and specific to that patient.

The ability to rapidly sequence the genome of a tumour using any next-generation sequencing technique, allows the identification of biologically significant mutations within the mutanome. Targeting an immunotherapy to these neoepitopes unique to the patient's tumour should result in an effective therapy tailored to the patient. Antigenic sequences of these biologically significant mutant peptides thus represent attractive peptides for conjugation to the adjuvant compounds of Formula (I).

Within the context of the invention, a peptide for conjugation may comprise additional amino acids than the ones originating from an antigen or may entirely be made of or consist of an amino acid sequence originating from such antigen. The length of the contiguous amino acid sequence from one of the above-defined antigens comprised within the peptide, preferably is at least 19, 20, 21, 22, 23, 24, 25, 26, 27, 28, 29, 30, 31, 32, 33, 34, 35, 36, 37, 38, 39, 40, 41, 42, 43, 44 or 45 amino acids and/or preferably no more than 100, 99, 98, 97, 96, 95, 94, 93, 92, 91, 90, 89, 88, 87, 86, 85, 84, 83, 82, 81, 80, 60, 50, 45, 40, 35, 33 or 30 amino acids, more preferably the length of the contiguous amino acid sequence from one of the above-defined antigens comprised within the peptide is 19-45, even more preferably 22-40 amino acids, even more preferably 30-35 and most preferably 33-35 amino acids. In another preferred embodiment, the peptide of the invention consists of any of the contiguous amino acid sequence from the antigen as defined herein, whereby it is understood that no amino acids are appended to either end of the contiguous amino acid sequence from the antigen that are not contiguous with this amino acid sequence in the sequence of the native antigen. These peptides may be easily synthesized and are large enough to be taken up by professional antigen presenting cells, processed by the proteasome and other proteases and peptidases of the intracellular processing system, and have sufficient physical capacity and length to contain at least one HLA class I and/or at least one HLA class II epitope. Optionally a peptide may comprise N- or C-terminal extensions, which may be additional amino acids, modified amino acids or other functional groups that may for instance enhance bioavailability, cellular uptake, targeting to T-cells, processing and/or solubility or comprise or release immune modulating substances that provide adjuvant or (co)stimulatory functions.

Vaccines

The compounds and conjugates described above are suitably used as part of a medicament or vaccine. The invention is thus directed to a compound or conjugate or a composition comprising a compound or conjugate for use as a medicament, preferably a medicament to treat a disease or condition as defined herein.

More preferably the invention is directed to a compound or conjugate or a composition comprising a compound or conjugate to induce or enhance a TLR-2 mediated innate immune reaction in a patient, preferably a mammal, more preferably a human.

The compound or conjugate may be used in a so-called mono-therapy wherein in a stand-alone treatment the existing immune system is stimulated, for example for local administration in the lymphoid drainage area of a tumor. Other standalone applications include the treatment of damage or disease of the central nervous system such as axon regeneration of (optic) nerves preferably by injection into the eye and treatment of ischemia such as ischemia of the heart or brain or other organs preferably by systemic injection. A further standalone application is the treatment of infections such viral, bacterial, fungal, protozoa and parasite infections such as visceral leishmanias and visceral endophtalmitis.

A compound for use in therapy may already comprise an antigen, for example a peptide or carbohydrate antigen and/or another compound such as an antibody, a nucleic acid such as a polynucleotide and an oligonucleotide, i.e. be a conjugate as defined herein. Alternatively or in combination with a previous embodiment, a composition comprising a compound as identified herein may further comprise an antigen, for example a peptide or carbohydrate antigen, and/or another compound such an antibody, a nucleic acid such as a polynucleotide and an oligonucleotide, as defined herein as a separate molecule.

The invention is therefore also directed to a compound comprising an antigen, for example a peptide or carbohydrate antigen, and/or another compound such as an antibody, a nucleic acid such as a polynucleotide and an oligonucleotide, and/or a composition comprising said compound or a composition comprising a compound and an antigen, for example a peptide or carbohydrate antigen, and/or another compound such as an antibody, a nucleic acid such as a polynucleotide and an oligonucleotide, as a separate molecule for use as a medicament, preferably as a preventive or therapeutic vaccine composition.

In particular, the invention is directed to a vaccine composition comprising the compound according to the invention as an adjuvant and at least one antigen, for example a peptide or carbohydrate antigen, and/or another compound such as an antibody, a nucleic acid such as a polynucleotide and an oligonucleotide, wherein the antigen or other compound may be present as a separate compound or conjugated to the compound according to the invention as described above. Preferably the antigen or other compound is part of the compound according to the invention, wherein the antigen or other compound is conjugated to the adjuvant compound described above. Such a linkage has the advantage that, in use, an enhanced immune response by simultaneous stimulation of antigen presenting cells, in particular dendritic cells, that internalize, metabolize and display antigen is achieved.

Therapeutic Uses

Compounds of the present invention are as defined by Formula (I) and have been shown to be agonists of the TLR-2 receptor, and thus behave as an adjuvant. An adjuvant is defined herein as a molecule which is able to stimulate the immune system in such a way that an immune response, or an increase thereof, is elicited against said antigen when the antigen is administered in combination with the adjuvant (as a single conjugate or as two separate molecules as defined herein). To analyze or assess the antigen-specific elicited immune response, said immune response is compared to the immune response induced in presence of the antigen without the adjuvant or in the presence of the antigen with a known adjuvant. A known adjuvant may be another TLR-2 adjuvant as identified in the experimental part. The induction is assessed in a subject or in cells from a subject.

The compounds and conjugates described herein are therefore useful in treatment or prevention of diseases as described herein in which an enhanced immune response may be beneficial.

Accordingly there is provided a method for the induction, maintenance and/or enhancement (boost) of an immune response in a subject against an antigen and/or for the prevention, delay and/or treatment of a disease or condition associated with said antigen in a subject wherein a compound, conjugate or a composition as defined herein is administered to said subject.

The subject may have or may be susceptible to cancer, an infectious disease, a non-autoimmune metabolic or degenerative disease or an atopic disease.

The antigen may be any material that can induce, maintain or enhance an immune response by the immune system of a subject. It is to be understood that said induced or enhanced immune response is specific for said antigen. An antigen-specific immune response is preferably a T cell response or cellular immune response. Such antigen therefore preferably comprises a T cell epitope: a T helper and/or a CTL epitope.

The immune response may be a B cell response, i.e. production of an antibody specifically directed against the antigen. The antibody may be an IgG antibody.

The B and/or T cell response may be detected by measuring the production of antibody and/or cytokine using an ELISA as described in the example. Preferred cytokines are IFNγ, IL-2, IL-4, IL-5, IL-8, IL-10, IL-12 or TNFα.

The detection of the antigen-specific elicited immune response means that said detection occurs after at least one, ten, eleven, twelve hours or more or after at least one day of administration of said adjuvant and antigen, or at least two days, or at least three days, or at least four days, or at least five days, or at least six days, or at least seven days, or at least two weeks, or at least three weeks, or at least 4 weeks or more. The detection is assessed in a subject or in cells from a subject.

In the context of the invention, the antigen-specific elicited immune response preferably means a detectable increase of an immune response against said antigen. Said detectable increase may be assessed by comparison with the immune response induced or elicited when the antigen is used alone or when said antigen is used with a known adjuvant. A known adjuvant may be another TLR-2 adjuvant as identified in the experimental part. A detectable increase is preferably an increase of at least 5% of the amount of a cytokine as already identified herein, or 10%, 15%, 20%, 25%, 30%, 35%, 40%, 45%, 50%, 55%, 60%, 65%, 70%, 75%, 80%, 85%, 90%, 95%, 100%, 150%, 200% or more after at least one, ten, eleven, twelve hours or more or after at least one day of administration of said adjuvant and antigen, or at least two days, or at least three days, or at least four days or more. The detection is assessed in a subject or in cells from a subject.

An antigen can be a full length biomacromolecule or a fragment thereof as described herein in connection with the functional groups of the compounds and conjugates. The antigen can for example be synthetic material, purified subunits of a protein, a protein fragment, a digest of a protein, a peptide, a DNA molecule, a cDNA molecule, a RNA molecule, an oligonucleotide, an oligosaccharide, a crude composition, preferably of biological origin such as a whole microbe, a bacterial, yeast or fungal lysate, sonicate or fixate or a mixture thereof. In an embodiment, when an antigen is a peptide, said peptide may be from 6 to 60 amino acids, or 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acids or more. In said embodiment, said peptide is therefore distinct from the protein it derives from.

An antigen may be a tumor antigen, viral antigen, bacterial antigen or parasite antigen. An antigen may be derived from an infectious agent. Such infectious agent may cause cancer and/or a premalignant condition. Thus, the disease or condition may be selected from cancer, a viral infection, a bacterial infection or a parasitic disease.

Preferably the antigen is a chemically synthesized or enzymatically produced peptide, oligonucleotide or oligosaccharide and more preferably it has been obtained after purification.

An antigen may also be in the form of a nucleic acid (DNA, or RNA) as described herein, the nucleic acid encoding said antigen or fragment thereof. The RNA or DNA molecules may be 'naked' DNA, preferably comprised in vesicles or liposomes, or they may be comprised in a vector. The vector may be any (recombinant) DNA or RNA vector known in the art, and preferably is a plasmid; wherein said DNA encoding said antigen is operably linked to regulatory sequences conferring expression and translation of the encoded messengers. The vector may also be any DNA or RNA virus, such as, but not limited to, Adenovirus, Adeno-Associated Virus (AAV), a retrovirus, a lentivirus, modified Vaccinia Ankara virus (MVA) or Fowl Pox virus, or any other viral vector capable of conferring expression of polypeptides into a chosen subject. DNA vectors may be non-integrating, such as episomally replicating vectors, or may be vectors integrating in the host genome by random integration or by homologous recombination.

The antigen is preferably selected as a single or multiple component from the group consisting of a protein of a pathogen, a recombinant protein, a peptide, a hapten, a polysaccharide, a glycoprotein, a lipopolysaccharide, a DNA molecule, a cDNA molecule, an RNA molecule (all polynucleotides), a cancer cell and a micro-organism.

A preferred composition comprises a compound according to the invention as adjuvant and at least one viral antigen or bacterial antigen, for example TBC; tetanus and *Helicobacter Pylori*, or parasite antigen or tumor antigen suitable for treating or preventing viral or parasitic or bacterial infections or treating or preventing cancer, or comprises a conjugate according to the invention, in which $R_3$ of Formula (I) is selected from —C(O)—$R_5$, —C(O)—$OR_6$, and —C(O)—$NHR_6$, in which $R_5$ or $R_6$ comprises a viral antigen or bacterial antigen, for example TBC and tetanus, or parasite antigen or tumor antigen suitable for treating or preventing viral or parasitic or bacterial infection or treating or preventing cancer.

Viral diseases or infections from which suitable viral antigens may be derived include diseases or infections caused by influenza virus, such as for example HA: haemaglutinin or neuraminidase antigen; human papilloma virus (HPV), such as E2, E6, E7 antigens; human immunodeficiency virus (HIV), such as for example GP120, GP140, GP160 antigens; vesicular stomatitis virus, for example vesicular stomatitis virus glycoprotein antigen; cytomegalovirus (CMV); hepatitis virus, such as for example hepatitis A(HAV), B(HBV), C(HCV), D(HDV) and G(HGV) antigens: L-HBsAg, S-HBsAg, M-HBsAg, pre S; respiratory syntytial virus (RSV); SV40 virus, such as Large T, small T antigens; EBV, such as EBNA antigen, Kaposi Sarcoma Virus (KSV), Human T-Lymphotropic Virus-1 (HTLV-1), Merkel cell virus (MCV) or herpes simplex virus.

In the example in which the viral infection is caused by HPV, the HPV strain from which the antigen or peptide used is derived is preferably a high risk HPV serotype, such as serotypes 16, 18, 31, 33 or 45, more preferably from the serotype 16, 18, 31 or 33, most preferably from serotype 16 or 18, of which 16 is most preferred.

Parasitic diseases or infections from which suitable parasite antigens may be derived include diseases or infections caused by protozoa, nematoda, trematoda or cestoda, such as *Cryptosporidium hominis* or *parvum; Schistosoma haematobium, mansoni* or *japonicum; Plasmodium falciparum, malariae, vivax* or *ovale; Leishmania major, tropica, aethiopica, mexicana, donovani, infantum* or *braziliensis; Toxoplasma Gondii*.

Bacterial diseases or infections from which suitable bacterial antigens may be derived include *Mycobacterium Tuberculosis, Streptococcus pneumoniae, Staphylococcus Aureus, Vibrio cholera, Neisseria meningitides*.

The vaccine compositions comprising compounds or conjugates as described herein may be used as preventive (i.e. prophylactic) or therapeutic (i.e. curative) vaccine compositions for acute or persistent infections or diseases caused thereby.

One example of a disease or condition which may be treated by the compounds and/or conjugates of Formula (I) is cancer. A cancer may be a non-viral cancer or a viral cancer such as a cancer induced by HPV and may be targeted therapeutically via a tumor antigen.

Tumor antigens are antigens expressed on tumor cells. This group of antigens is preferably said to be associated with cancer in the following illustrating and non-limitative cases: antigens derived from proteins that are expressed solely on tumors and not or only in a limited amount on normal adult cells, antigens derived from proteins that are over-expressed on tumors as compared to normal adult cells, antigens derived from proteins that have been mutated in tumors, antigens that are aberrantly expressed in a given tissue of cancer patients by comparison with the corresponding tissue of a subject not having cancer. An aberrantly expressed antigen may be de novo expressed in a tissue wherein it is normally not expressed. A mutated antigen may be a splice variant. A mutated antigen may further be produced as an aberrant fusion protein as a result of a translocation.

A preferred vaccine composition comprises a compound according to the invention as adjuvant and at least one viral or non-viral cancer-associated tumor antigen or comprises a conjugate according to the invention, wherein group $R_3$ of Formula (I) is selected from —C(O)—$R_5$, —C(O)—$OR_6$, and —C(O)—$NHR_6$, in which $R_5$ or $R_6$ comprises a viral or non-viral cancer-associated tumor antigen.

The cancer to be treated or be prevented may be a brain cancer, renal cell carcinoma, a melanoma, a leukemia, a lung cancer, a stomach cancer, an esophageal cancer, a thyroid cancer, a pancreatic cancer, a breast cancer, a prostate cancer, an ovarian cancer, a uterine cancer, a testicular cancer, a cholangioma, a liver cancer, a colon cancer, a gastrointestinal cancer, a bladder cancer, or a rectal cancer. In addition pre-malignant lesions may be treated or prevented by use of the vaccine composition. Pre-malignant lesions are lesions that have undergone genetic changes that predispose cells to become cancer cells. These pre-malignant lesions may evolve into cancers over time.

Examples of suitable tumor antigens are gp100, MART-1, MAGE-1, BAGE, GAGE, HAGE, tyrosinase, CEA (cancer embryonic antigen), p53, MDM-2, HDM2 and other proteins playing a role in p53 pathway, PSA (prostate specific antigen), PSMA (prostate specific membrane antigen); PRAME, HER2/neu, MAGE-1, MAGE-2, MAGE-3, NY-ESO-1, MUC-1, SART-1 or SART-3, XAGE-1B, Tyrosinase, TERT (telomerase reverse transcriptase), WT1, Survivin-2B, gp75, telomerase, al[rho]h-1 fetoprotein, CA125, CA15-3, CA19-9, G250, HER2, CD19 BCR-ABL, Ras, PML-RARα, PR1, SSX-2, HSP70.

Suitable tumour antigens also include antigens derived from infectious agents that cause cancers and/or premalignant conditions. Examples of such infectious agents are HPV, which causes diseases such as genital warts, a cervical cancer, head and neck cancer, Penile cancer, Vulva cancer, Anal cancer, nasopharyngeal cancer, CIN, VIN, PIN, VAIN and AIN, HCV and HBV, which are involved in liver carcinoma, SV40, which is involved in mesothelioma, HTLV-1, which is involved with T cell leukemia/lymphoma, Merkel cell virus, which is involved with Merkel cell carcinoma and KSV, which is involved with Kaposi sarcoma.

In another example, a tumour antigen comprises a peptide or an antigenic fragment thereof which is derived from a subject's mutanome. The antigen derived from a subject's mutanome may be any tumour antigen described previously, or any other tumour antigen differentially expressed in the patient's mutanome relative to the patient's normal cells. A subject-derived tumour antigen may be identified through biopsy and genome sequencing to identify mutant proteins within the subject tumour's mutanome, and subsequent identification of an antigenic portion of the mutant portion through standard techniques.

Salts, Solvates, Prodrugs

The compounds and conjugates described herein may be further defined with reference to corresponding salts, solvates and prodrugs.

The term "salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts. Examples of preferable inorganic acid salts include: hydrochloride, hydrobromate, sulfate, nitrate, and phosphate. Examples of preferable organic salts include: acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples of preferable organic base salts include: diethylamine salts, diethanol amine salts, meglumine salts, and N,N'-dibenzylethylenediamine salts. Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention.

A solvate can include also water together with the one or more organic solvent.

Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of Formula (I) may be used in the present invention. "Pharmaceutically acceptable prodrugs" means those prodrugs of the compounds which are, within the scope of sound medical and vetinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above Formula, for example by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press, 1987, which are incorporated herein by reference.

Compositions and Administration

The compound according to the present invention may be administered in the form of a composition comprising the adjuvant or peptide-adjuvant conjugate and any suitable additional component. The composition may, for example, be a pharmaceutical composition (medicament), suitably for enteral administration (e.g. as a tablet or capsule or drop) or parenteral administration (e.g. injection, implantation or infusion) or topical administration (e.g. as eyedrops or cream or lotion). The composition may alternatively, for example, be a foodstuff, food supplement, beverage or beverage supplement.

The term "pharmaceutical composition" or "medicament" in the context of this invention means a composition comprising the compound or conjugate and comprising additionally one or more pharmaceutically acceptable carriers. The composition may further contain ingredients selected from, for example, diluents, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of liquid preparations for injections, including liposome preparations, or tablets, dragees, powders, elixirs, syrups, liquid preparations including suspensions, sprays, inhalants, tablets, lozenges, emulsions, solutions, cachets, granules, capsules and suppositories for enteral administration. Techniques and formulations generally may be found in Remington, The Science and Practice of Pharmacy, Mack Publishing Co., Easton, PA, latest edition.

The composition may comprise additional adjuvants, in addition to the adjuvant compound (or adjuvant part of the conjugate). These other adjuvants may be admixed to the composition or may be administered separately. Examples of suitable other adjuvants to be used in combination with the adjuvant compound according to the invention are Montanide adjuvant, such as Montanide ISA-51 or Montanide ISA 720 (Seppic France), Freund's adjuvant or IFA, Resiquimod; imiquimod; Poly IC:LC (Hiltonol); ISCOMS; CpG and GLA; MPL. Another adjuvant is a T cell adhesion inhibitor, more preferably an inhibitor of an endothelin receptor such as BQ-788 (Buckanovich R J et al, Ishikawa K, PNAS (1994) 91:4892).

The composition may also comprise compounds such as detoxified Lipid A, clinical grade CpG or other appropriate immunomodulatory agent or antibody such as CTLA-4 blocking or CD40 agonistic antibodies or agonistic antibodies against other members of the TNF receptor family such as OX40, CD27, 4-1-BB (CD137) or 4-1-BB and/or CD40 ligands, OX40 ligands or functional fragments and derivates thereof, as well as synthetic compounds with similar agonistic activity. These compounds can be mixed or conjugated to either the compound according to the invention and/or to the specific antigen in the vaccine.

Liquid form preparations include solutions, suspensions, and emulsions are particularly preferred. A pharmaceutically acceptable liquid carrier can be selected or be prepared by mixing one or more ingredients from saline, sterilized water, Ringer's solution, buffered saline, dextrose solution, maltodextrose solution, glycerol and ethanol. As an example may be mentioned water or water-propylene glycol solutions for parenteral injection or topical administration. Liquid preparations can also be formulated in solution in aqueous polyethylene glycol solution.

Also included are solid form preparations which are intended to be converted, shortly before use, to liquid form preparations for either topical, oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for topical or parenteral use.

In a preferred embodiment, the vaccine composition is formulated to be suitable for intradermal administration or application. Intradermal is known to the skilled person. In the context of the invention, intradermal is synonymous with intracutaneous and is distinct from subcutaneous. A most superficial application of a substance is epicutaneous (on the skin), then would come an intradermal application (in or into the skin), then a subcutaneous application (in the tissues just under the skin), then an intramuscular application (into the body of the muscle).

The intradermal administration of the vaccine composition is very attractive since the injection of the vaccine is realized at or as close by as possible to the site of the disease resulting in the local activation of the disease draining lymph node, resulting in a stronger local activation of the immune system. In a preferred embodiment, the intradermal administration is carried out directly at the site of the lesion or disease. At the site of the lesion is herein understood to be within less than 5, 2, 1, 0.5, 0.2 or 0.1 cm from the site of the lesion.

In addition, a preferred embodiment comprises delivery of the antigen and adjuvant compound, or conjugate, as part of the vaccine composition in a slow release vehicle such as mineral oil (e.g. Montanide ISA 51), PLGA based particles or scaffolds, dextran based particles or scaffolds, poly active based particles or scaffolds, liposomes, virosomes. Preferably for intradermal delivery the vaccine composition is administered in a composition comprising in addition one or more immunologically inert pharmaceutically acceptable carriers, e.g. buffered aqueous solutions at physiological ionic strength and/or osmolarity (such as e.g. PBS).

It is furthermore encompassed by the present invention that the administration of at least one vaccine composition of the invention may be carried out as a single administration. It may also be possible that the various active compounds of the vaccine are administered sequentially and/or using different ways or different sites of administration. Alternatively, the administration of at least one vaccine composition may be repeated if needed.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired. The compound of Formula (I) or a pharmaceutically acceptable salt, solvate, hydrate or prodrug thereof may be administered in a therapeutically effective amount.

The dosage regime for administration of a compound or conjugate of Formula (I) may, for example, comprise a total dose of up to 1 µg, for example up to 500 ng, for example up to 50 ng, for example less than 20 ng of compound or conjugate of Formula (I) in a dosing period ranging, for example, between 1 and 14 days. For example, a total dose of less than 18 ng, 17 ng, 16 ng, 15, ng, 14 ng, 13 ng, 12 ng, 11 ng or 10 ng may be administered.

The dosage regime for administration of a compound or conjugate of Formula (I) may, for example, comprise a total dose of up to 10 µg, for example up to 5 mg, for example up to 500 ng, for example less than 200 ng of compound or conjugate of Formula (I) in a dosing period ranging, for example, between 1 and 14 days. For example, a total dose of less than 180 ng, 170 ng, 160 ng, 150 ng, 140 ng, 130 ng, 120 ng, 110 ng or 100 ng may be administered.

The dosage regime for administration of a compound or conjugate of Formula (I) may, for example, comprise a total dose of up to 10 mg, for example up to 5 mg, for example up to 500 µg, for example less than 200 µg of compound or conjugate in a dosing period ranging, for example, between 1 and 14 days. For example, a total dose of less than 180 µg, 170 µg, 160 µg, 150 µg, 140 µg, 130 µg, 120 µg, 110 µg or 100 µg may be administered.

The compound or conjugate of Formula (I) or a pharmaceutically acceptable salt, solvate, hydrate or prodrug thereof may be administered in a therapeutically effective amount. A therapeutically effective amount of a compound or conjugate of Formula (I) may be at least about 5 µg/10 µl of delivery vehicle. Alternatively, a therapeutically effective amount may be at least about 100 µg/mL, for example at least about 200 µg/mL, at least about 300 µg/mL, at least about 400 µg/mL, at least about 500 µg/mL, at least about 600 µg/mL, at least about 700 µg/mL, at least about 800 µg/mL, at least about 900 µg/mL, or at least about 1000 µg/mL, Alternatively, a therapeutically effective amount may be at least about 1 mg/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1 mg/mL. The therapeutically effective amount may be administered daily, for a dosing period ranging, for example, between 1 and 14 days. The therapeutically effective amount may be a total daily dosage which may be divided and administered in portions during the day, for example twice daily.

"Treating or Preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

"Susceptible to"

The expression "susceptible to" and analogous terms used herein refers particularly to individuals at a higher than normal risk of developing a medical disorder, as assessed using the known risk factors for the individual or disorder. Such individuals may, for example, be categorised as having a substantial risk of developing one or more particular disorders, to the extent that prophylactic medication would be prescribed.

Examples would include an individual's increased susceptibility to oncogenesis (development of cancer) following HPV infection.

Kit-of-Parts

Described herein is a kit-of-parts, comprising: a compound or a conjugate as described herein; and a therapeutic agent selected from a chemotherapeutic agent, an anti-inflammatory agent, an anti-viral agent and an antigen to which an immune response is required.

The kit may further contain instructions for administering the compound or conjugate and the therapeutic agent to a subject in need thereof, for the treatment or prevention of a disease, disorder or condition to which an immune response is required, as described herein.

The kit may further contain packaging, which may comprise a label or packaging insert containing the instructions and medical indications for which the kit is to be used. The kit may comprise only one of the compound or conjugate and the therapeutic agent, with the instructions indicating that it is to be used in combination with the other of the compound or conjugate and the therapeutic agent.

Methods

Synthetic Protocol

The synthetic protocol for compounds of the present disclosure is shown in Scheme 1, with full experimental details for each step described in detail below. Variations of this protocol to synthesize other compounds or conjugates within the scope of the present disclosure are within the wherewithal of the skilled person.

Scheme 1
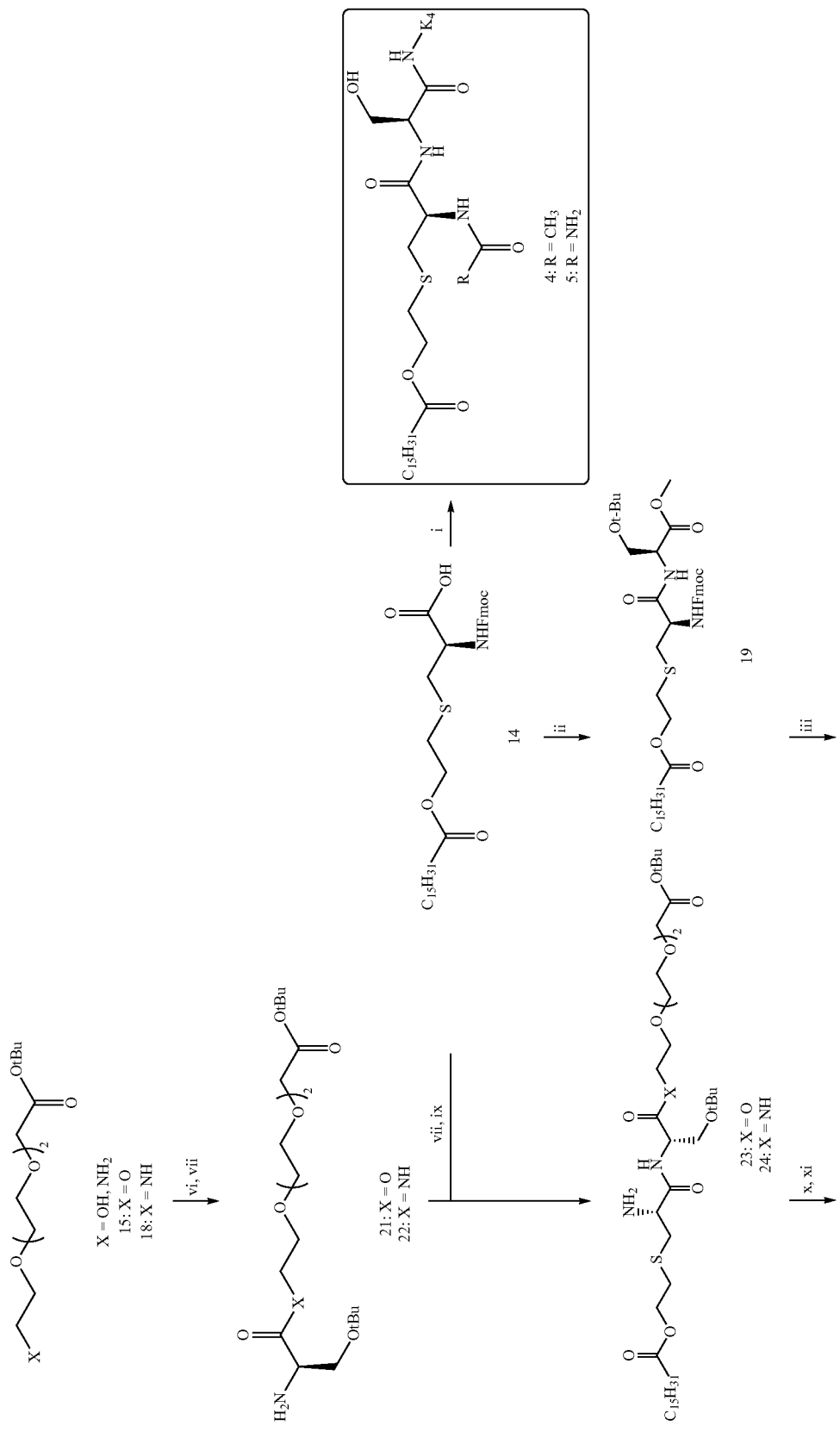

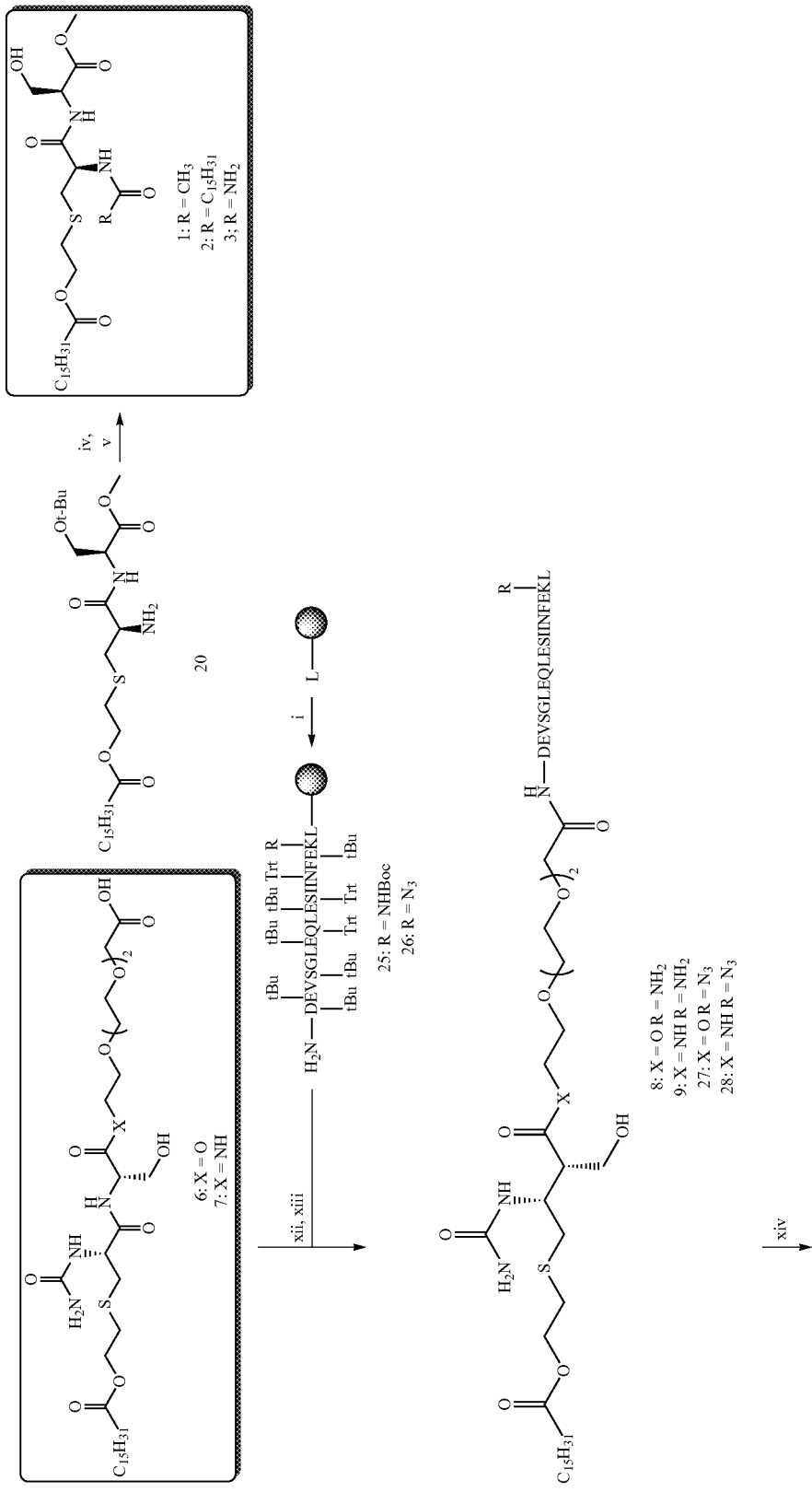

-continued

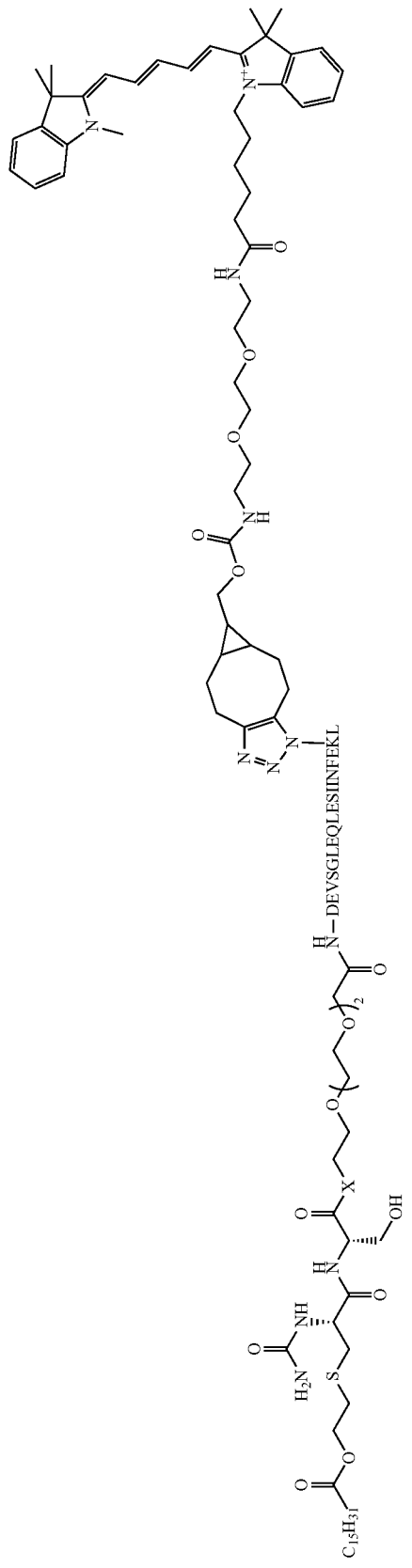

10: X = O
11: X = NH i) SPPS Fmoc peptide synthesis; TFA/H₂O/TIS(95/2.5/2.5) ii) H-Ser(tBu)—OMe·HCl, DIC, HOBt, Et₃N, DCM, 88% iii) 2% Piperidine, DMF, RT, 88% iv) R = Ac, Acetic anhydride, TEA, DCM, RT, 94%; R = C₁₅H₃₁ Palmitoyl chloride, pyridine, RT, qt.; v) TFA, RT, 62-94% vi) Fmoc-Ser(tBu), DIC, HOBt, DCM, rt, X = OH: qt., X = NH₂: 47% vii) 2% DBU, 2% piperidine, DMF, RT, X = O: 76%, X = NH: qt. viii) DIC, HOBt, DCM, RT, X = O: 71%, X = NH: qt. ix) DBU, octanethiol, DCM, RT, X = O: 90%, X = NH: 88% x) TMS i-CN, i-PrOH, DCM, RT, X = O: 90%, X = NH: 82% xi) TFA/TIS/H2O 95:2.5:2.5, RT, X = O: 80%, X = NH: 82% xii) TFA/H₂O/TIS 95:2.5/2.5, xiii) HCTU, Dipea, NMP xiii) TFA/H₂O/TIS 95:2.5/2.5, xiv) Cy5-BCN, DMSO To arrive at the projected ligands and conjugates (Scheme 1 above and FIG. 1), attention was first directed to the synthesis of common cysteine derivative 14 (Scheme 2) and PEG spacers 15 and 18 (Scheme 3), as described below.

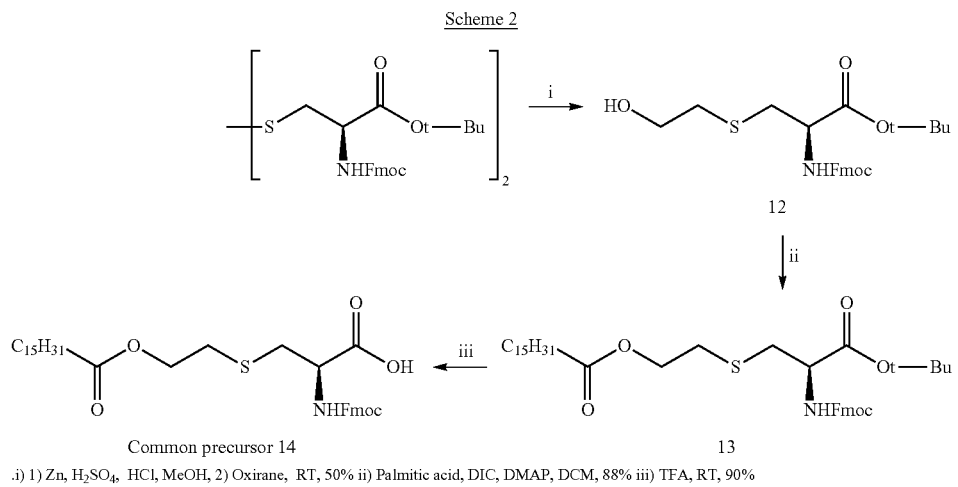

Scheme 2

Common precursor 14 i) 1) Zn, H$_2$SO$_4$, HCl, MeOH, 2) Oxirane, RT, 50% ii) Palmitic acid, DIC, DMAP, DCM, 88% iii) TFA, RT, 90%

In a one pot-procedure commercially available Fmoc-Cysteine-tBu was first reduced using activated zinc in an acidic environment and upon completion of the reduction oxirane was added at 0° C. to give alcohol 12 in 50% yield. Subsequent esterification of 12 with palmitic acid to 13 using diisopropyl carbodiimide (DIC) and DMAP proceeded smoothly. Finally the tBu ester in 13 was cleaved with neat TFA to give target cysteine derivative 14 in 40% overall yield.

15. The alkylation was accompanied by the formation of substantial amounts of bis-substituted product. The synthesis of the amino PEG spacer 18 began with mesylation of 15, followed by substitution with sodium azide to give compound 17. Staudinger reduction of the azide in 17 led to isolation of the amine PEG spacer 18 in a moderate yield.

Guided by the outcome of immunological evaluation, compounds 6 and 7 were coupled via an ester or amide linkage to MHC 1 epitope DEVSGLEQLESIINFEKL (SEQ ID NO: 1) to give conjugates 8 and 9, respectively. In addition, the corresponding labeled conjugates 10 and 11 were prepared.

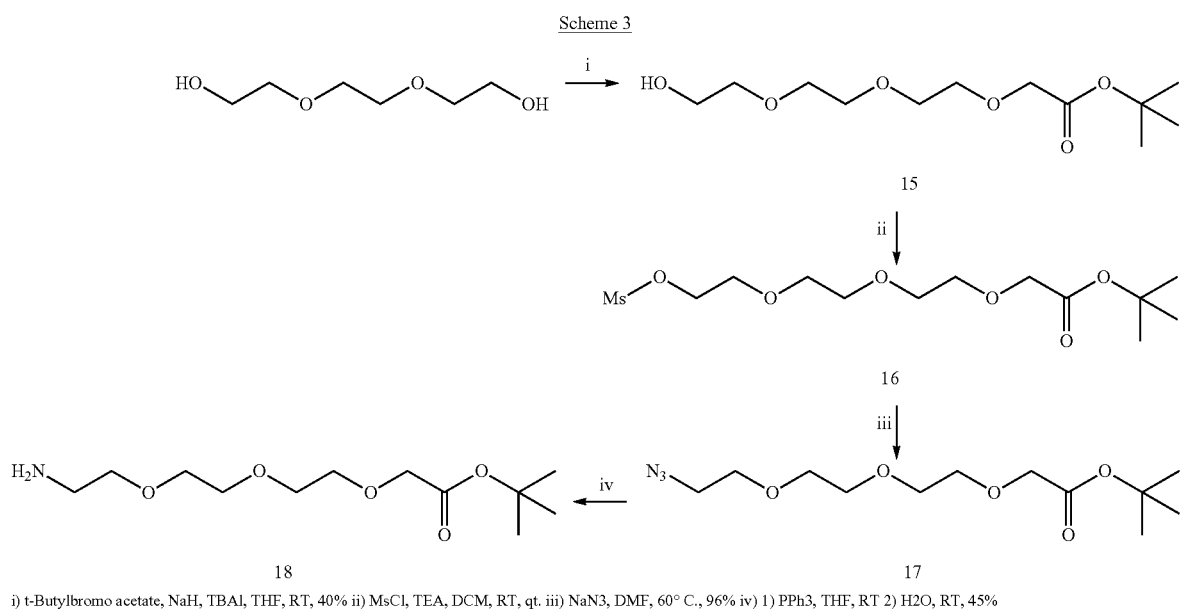

Scheme 3 i) t-Butylbromo acetate, NaH, TBAI, THF, RT, 40% ii) MsCl, TEA, DCM, RT, qt. iii) NaN3, DMF, 60° C., 96% iv) 1) PPh3, THF, RT 2) H2O, RT, 45%

The preparation of the PEG spacers, as illustrated in Scheme 3, started with a Williamson alkylation of triethylene glycol, with t-butyl bromoacetate in the presence of a catalytic amount of TBAI to yield the alcohol PEG spacer The reference ligands of the group of David (1 and 2) and the urea modified version 3 were prepared starting from cysteine derivative 14 (Scheme 2). In a standard procedure 14 was coupled with NH$_2$-Ser(tBu)-OMe using DIC and HOBt as coupling agents to give 19. Ensuing Fmoc cleavage with a mixture of piperidine and DBU in dry DMF to prevent cleavage of the methyl ester gave common precursor 20. Acylation of amine 20 with acetic anhydride or palmitoyl chloride, and subsequent cleavage of the tBu ether with neat TFA provided compounds 1 and 2, respectively. En route to modified version 3 the urea moiety was installed by treatment of 20 with TMS isocyanate in the presence of isopropanol. Although the role of isopropanol is unclear, it seems to be mandatory for the success of this reaction. Similarly, to the synthesis of 1 and 2, tBu ester was removed using neat TFA to afford ligand 3.

Cysteine derivative 14 was also used in the solid phase peptide synthesis (SPPS) to tetra-lysine containing ligands 4 and 5. With the aid of an automated peptide synthesizer and standard Fmoc chemistry immobilized $SK_4$ was prepared using Tentagel S RAM resin, Fmoc-Lys(Boc) and Fmoc-Ser(OtBu)-OH. Subsequent manual condensation of building block 14 with immobilized $SK_4$ under influence of PyBOP was followed by Fmoc removal to give the immobilized peptide having a free amine. Acetylation of this amine with acetyl chloride and TFA/TIS mediated protecting group removal and cleavage from the solid support led the isolation of ligand 4. Alternatively, the same immobilized peptide with a free amine was treated with TMS isocyanate as described for the conversion of 20 into 3 and subsequent TFA/TIS treatment gave after purification ligand 5.

The ligands 6 and 7 were prepared in solution phase. First PEG spacers 15 and 18 were elongated with a serine moiety by a DIC mediated condensation with Fmoc-Ser(tBu)-OH, followed by Fmoc cleavage to afford 21 and 22. Next cysteine derivative 14 was coupled to the free amine in 21 and 22 by the same sequence of events except that octanethiol was used as a scavenger during Fmoc cleavage. Installation of the urea moiety at the newly obtained amine was performed as described above and acidic cleavage of the tBu groups yielded ligands 6 and 7.

Having ligands 6 and 7 in hand the SPPS assembly of conjugates 8-9 and 27-28 was undertaken. Immobilized peptides 25 and 26, having a Boc protected lysine or an azidonorleucine incorporated were prepared with standard SPPS. Ligands 6 and 7 were appended manually by preactivation with HCTU. The progress of the reaction was monitored with the aid of the Kaiser test. Upon completion of the synthesis, removal of the protecting groups and cleavage from the resin with a TFA cocktail led after HPLC purification to the isolation of both the conjugates 8, 9 and the conjugates 27-28, having an azido group. Conjugates 27 and 28 were labelled with $Cy_5$-BCN in DMSO.

Figure 2A:
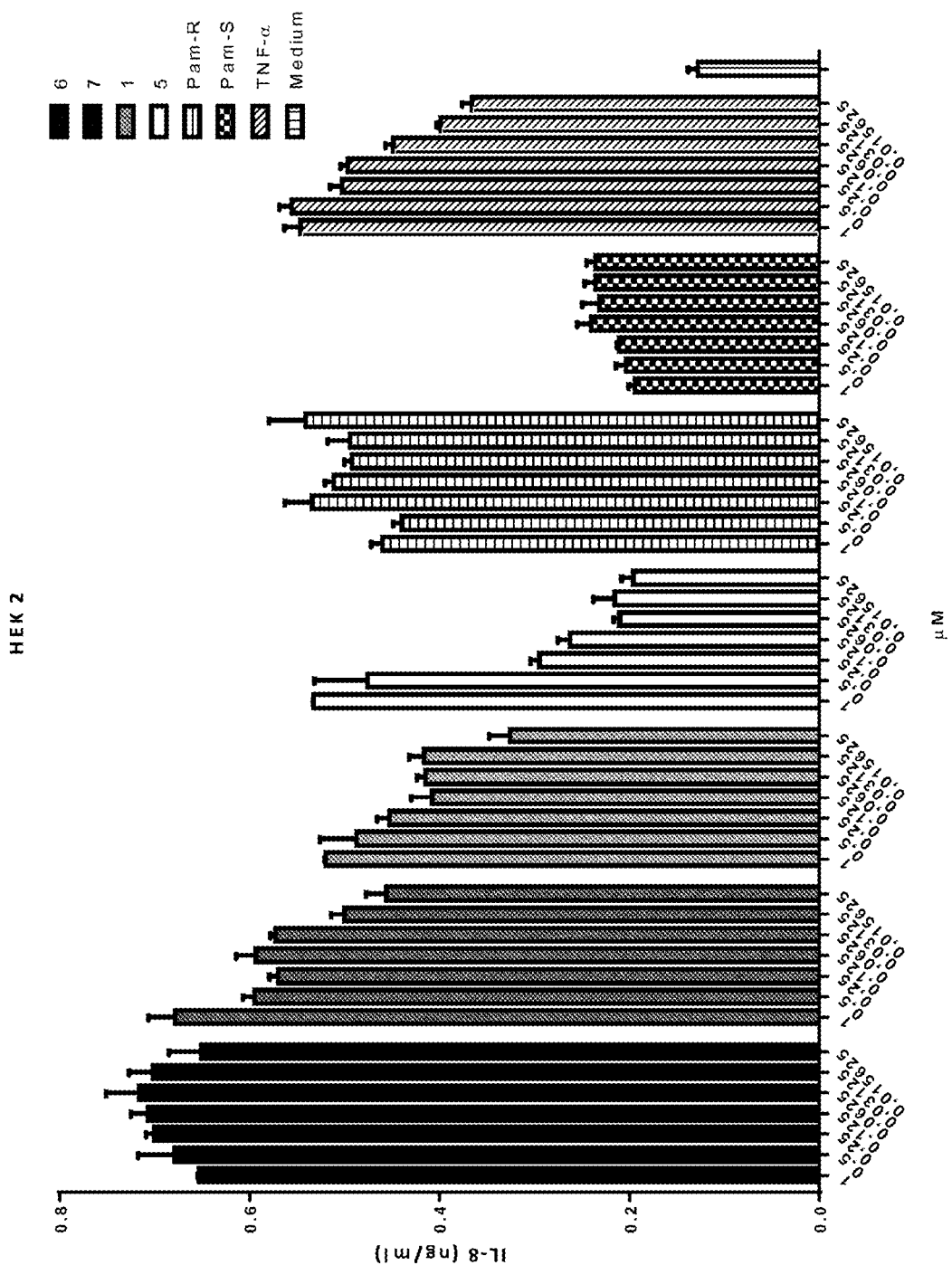
FIG. 2A demonstrates the ability of the lipophilic ligands in triggering human IL-8 production via TLR-2 (error bars represent SD)
Figure 2B:
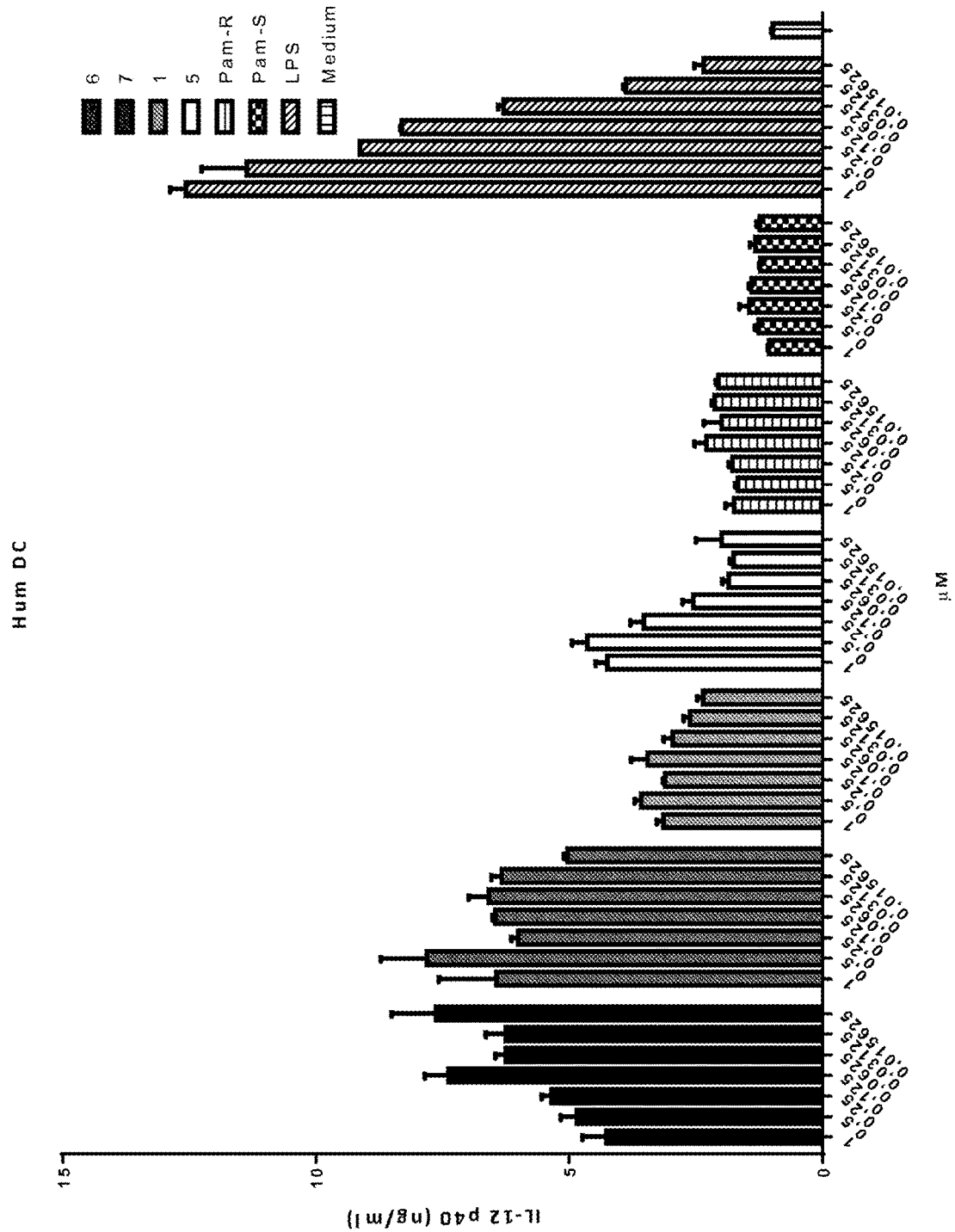
FIG. 2B demonstrates activation of human dendritic cells, determined by IL-12 cytokine secretion by ELISA analysis. One representative from three independent experiments is shown (error bars represent SD)
Figure 3A:
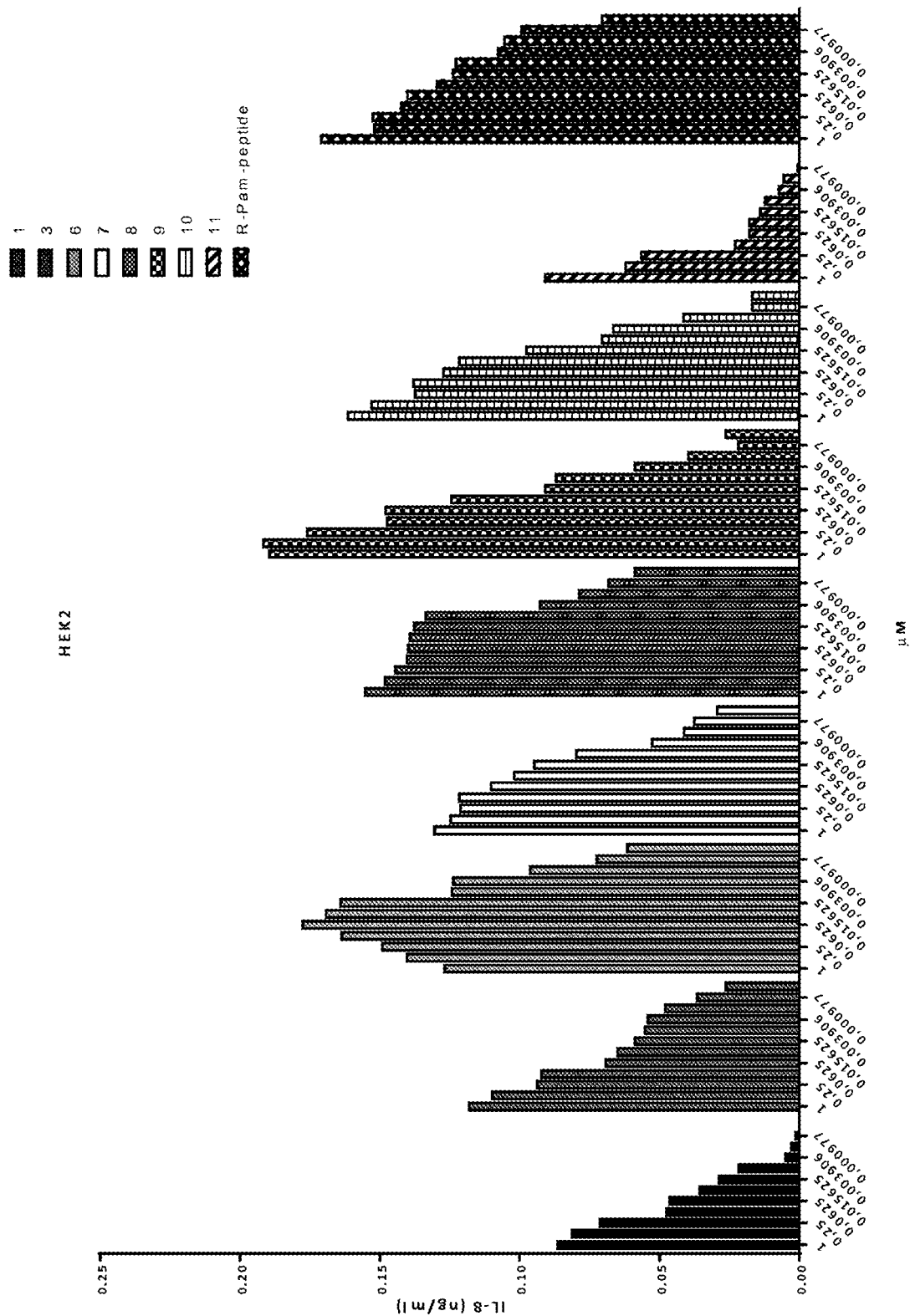
FIG. 3A demonstrates the ability of the lipophilic ligands and lipopeptides in triggering human IL-8 production via TLR-2. (a) HEK TLR-2 cells were incubated with titrated amounts of test compounds or controls for 24 h.
Figure 3B:
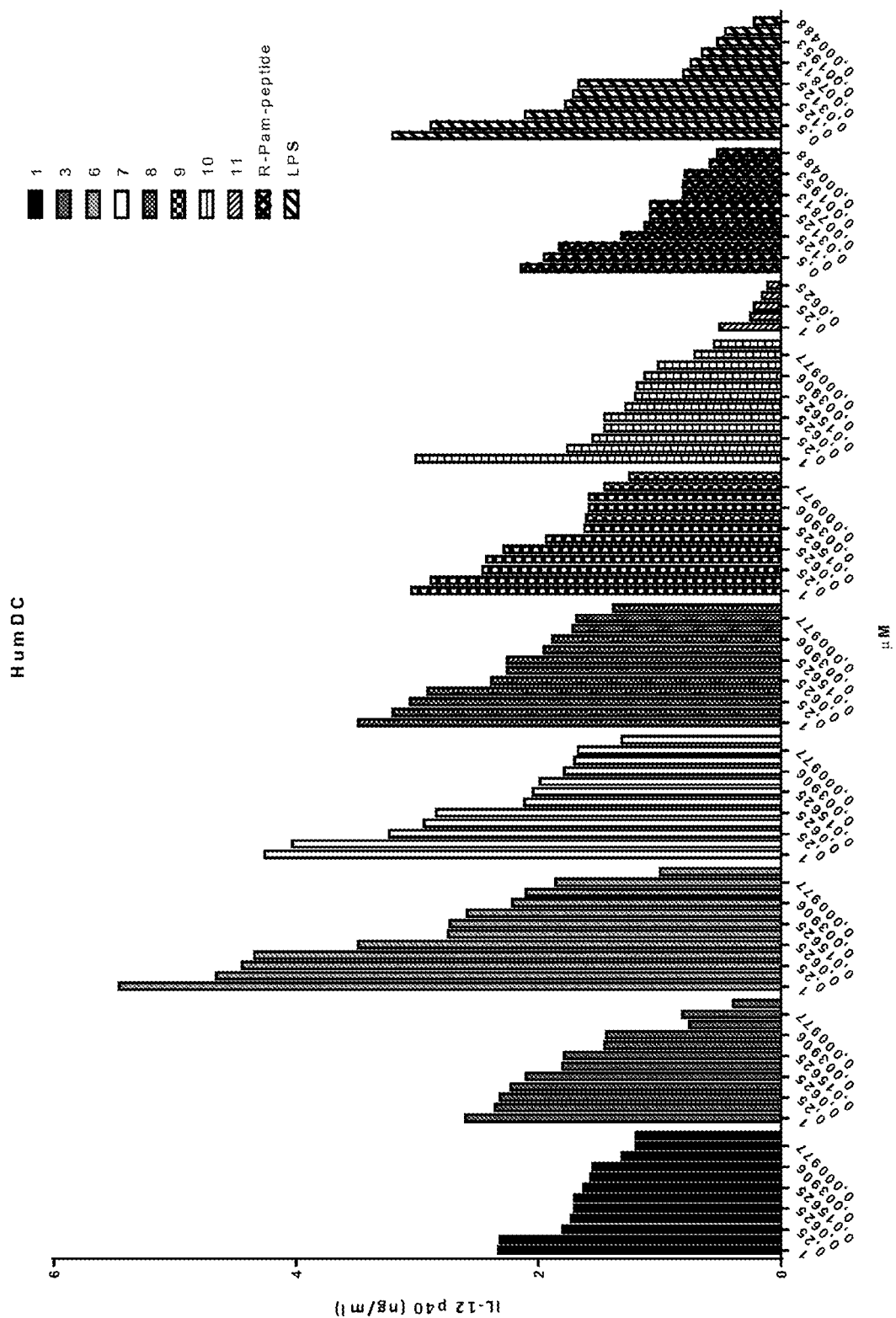
FIG. 3B demonstrates activation of human dendritic cells. DCs were stimulated with titrated amounts of test compounds or controls. Supernatants were harvested and analyzed for IL-12 cytokine secretion by ELISA as in FIG. 2B.

Immunological evaluation was performed on two different cell types, TLR-2 transfected HEK cells and isolated human DC. FIG. 2 shows that our modified ligands compounds 6 and 7 show excellent capacity to activate both TLR2 HEK cells (FIG. 2A) and human monocyte-derived dendritic cells (FIG. 2B). Their TLR2-mediated bio-activity was improved compared to the original ligand described by the David group (compound 1 and 5) and also compared to chirally pure Pam3 CSK4 (Pam-R). The compounds conjugated to antigenic long peptide sequences (compounds 8, 9 and the labeled compounds 10, 11) showed intact bio-activity on both HEK cells and human DC (see FIGS. 3A and 3B). These results show that the PEG spacer connecting the mono-Pam moiety to the peptide sequence retained strong bio-activity.

Figure 4A:
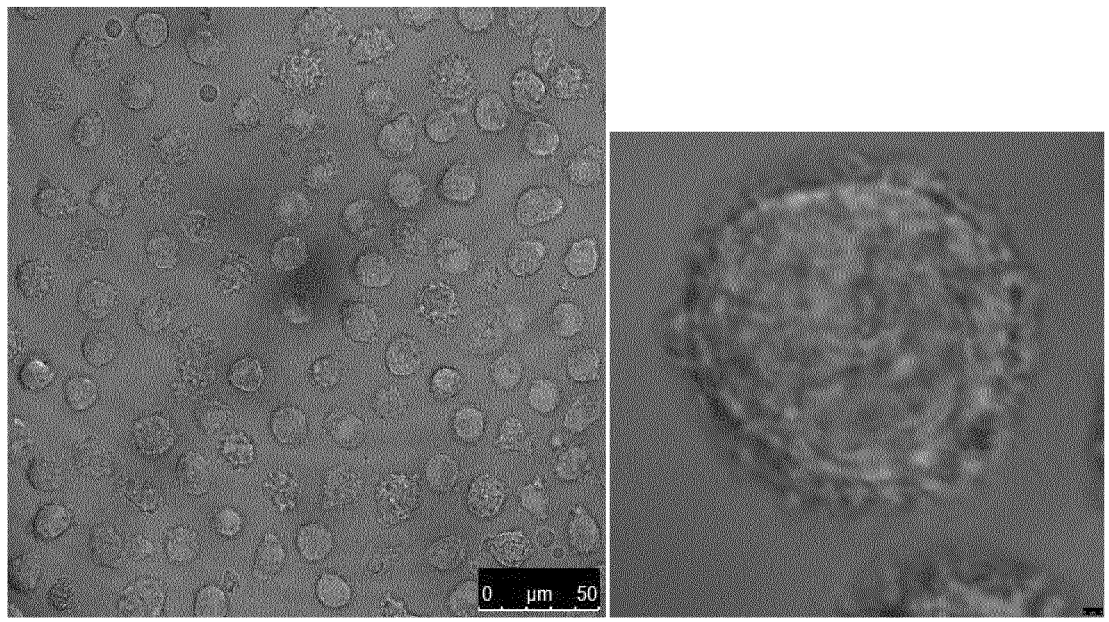
FIG. 4A demonstrates uptake of conjugate 10 by human moDC. The cells were incubated for 15 min with compound 10 (1 µM). The uptake and localization of the compounds were analyzed with confocal laser scanning microscopy. The images are representative for multiple cells in at least 3 experiments.
Figure 4B:
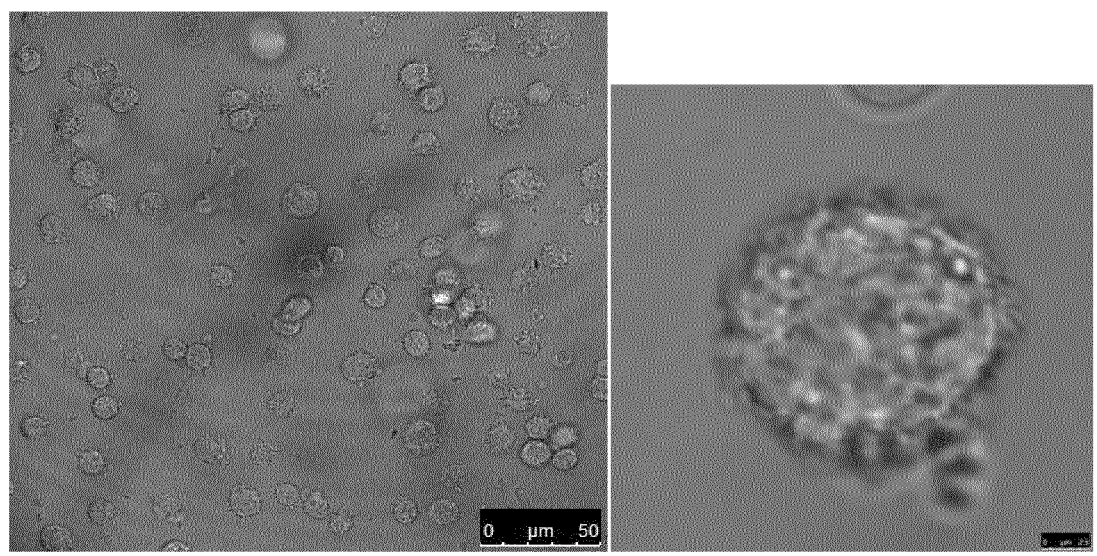
FIG. 4B demonstrates uptake of conjugate 10 by mouse D1-cells. The cells were incubated for 15 min with compound 10 (1 μM). The uptake and localization of the compounds were analyzed with confocal laser scanning microscopy. The images are representative for multiple cells in at least 3 experiments.

These conjugates were analyzed for dendritic cell uptake. Dendritic cell uptake was analyzed using the Cy5 fluorophore-labeled conjugate compound 10. FIG. 4 shows efficient engulfment of the compounds in both human (FIG. 4A) and murine dendritic cells (FIG. 4B) in endo-lysosomal compartments.

EXPERIMENTAL

All solvents used under anhydrous conditions were stored over 4 Å molecular sieves, except for methanol, which was stored over 3 Å molecular sieves. Solvents used for workup and column chromatography were of technical grade from Sigma Aldrich and used directly. Unless stated otherwise, solvents were removed by rotary evaporation under reduced pressure at 40° C. Reactions were monitored by TLC-analysis using Merck 25 DC plastikfolien 60 F254 with detection by spraying with 1% $KMnO_4$, 10% $Na_2CO_3$(aq) (unless stated otherwise) followed by charring at approx. 150° C. Column chromatography was performed on Fluka silicagel (0.04-0.063 mm). Analytical LC/MS was conducted on a JASCO system using an Alltima $C_{18}$ analytical column (5µ particle size, flow: 1.0 ml/min), on which the absorbance was measured at 214 and 254 nm. Solvent system for LC/MS: A: 100% water, B: 100% acetonitrile, C: 1% TFA. High resolution mass spectra were recorded by direct injection (2 µL of a 2 µM solution in water/acetonitrile; 50/50; v/v and 0.1% formic acid) on a mass spectrometer (Thermo Finnigan LTQ Orbitrap) equipped with an electrospray ion source in positive mode (source voltage 3.5 kV, sheath gas flow 10, capillary temperature 250° C.) with resolution R=60000 at m/z 400 (mass range m/z=150-2000) and dioctylpthalate (m/z=391.2842) as a "lock mass". The high resolution mass spectrometer was calibrated prior to measurements with a calibration mixture (Thermo Finnigan). $^1H$ and $^{13}C$ NMR spectra were recorded with a Brüker AV 400 (400/100 MHz) and all individual signal were assigned using 2D-NMR spectroscopy. Chemical shifts are given in ppm (δ) relative to TMS (0 ppm) and coupling constants are given in Hz. Optical rotations were measured in $CHCl_3$. IR spectra were recorded on a Shimadzu FTIR-8300 and are reported in $cm^{-1}$.

N-Fluorenylmethoxycarbonyl-S-[2 Hydroxy Ethyl]-(R)-cysteine Tert-Butyl Ester (12)

To a solution of protected cysteinedisulfide (1.04 mmol, 835 mg) in THF (10 mL) was added zinc powder (7 mmol, 455 mg, <10 µm) and a 100:7:1 solution of MeOH:37% HCl:98% $H_2SO_4$ (5 mL). The mixture was stirred for 15 min at RT. Oxirane (10 mmol, 0.51 mL) was added at 0° C. and the mixture was stirred overnight at RT. TLC analysis (2:8 EA:Pnt, $R_f$=0.7) showed complete conversion and the reaction mixture was filtrated and concentrated in vacuo. The crude was dissolved in EtOAc and washed with 10% $KHSO_4$(aq). The solution was dried ($MgSO_4$), filtrated and concentrated in vacuo. Purification by silica gel column chromatography (4:6 EA:Pnt, $R_f$=0.4) yielded compound 12 (1.07 mmol, 477 mg) in a 50% yield. IR ($cm^{-1}$): 2917, 2850, 1742, 1660, 1463, HRMS [M+H]$^+$: 444.18392 (calculated), 444.18436 (measured).

$^1H$ NMR (400 MHz, $CDCl_3$) δ 7.74 (d, J=7.5 Hz, 2H), 7.60 (d, J=7.3 Hz, 2H), 7.38 (t, J=7.4 Hz, 2H), 7.30 (t, J=7.4 Hz, 2H), 5.90 (d, J=7.9 Hz, 1H), 4.55-4.45 (m, 1H), 4.39 (m, 2H), 4.22 (t, J=7.0 Hz, 1H), 3.77-3.66 (m, 2H), 3.06-2.87 (m, 2H), 2.80-2.65 (m, 2H), 1.47 (s, 9H).

$^{13}$C NMR (101 MHz, CDCl$_3$) δ 169.75, 156.00, 143.85, 141.31, 127.75, 127.11, 125.15, 120, 83.04, 67.15, 60.90, 54.62, 47.14, 36.31, 35.04, 28.02,

N-Fluorenylmethoxycarbonyl-S-[2 Palmitoyloxy Ethyl]-(R)-cysteine Tert-Butyl Ester (13)

Compound 12 (2.23 mmol, 987 mg) was dissolved in dry DCM (30 mL). Palmitic acid (6.69 mmol, 1.72 g), DIC (8.92 mmol, 1.41 mL) and DMAP (1.1 mmol, 0.14 g) were added. The mixture was stirred overnight at RT under argon atmosphere. TLC analysis (4:6 EA:Pnt, R$_f$=0.4) showed complete conversion. Glacial acetic acid (1 mL) was added and the mixture was stirred for 15 min at RT. The reaction mixture was filtrated and concentrated in vacuo. The crude was dissolved in PE and filtrated. The filtrate was purified by silica gel column chromatography (5:95 EA:Pnt, R$_f$=0.15) and compound 9 (1.97 mmol, 1.34 g) was obtained with a 88% yield.

$[α]_D$: +2°
IR (cm$^{-1}$)=3333, 2916, 2850, 1733, 1699, 1532
HRMS [M+H]$^+$: 682.41354 (measured), 682.41359 (calculated).
$^1$H NMR (400 MHz, CDCl$_3$) δ 7.75 (d, J=7.5 Hz, 2H), 7.61 (d, J=7.3 Hz, 2H), 7.39 (t, J=7.4 Hz, 2H), 7.30 (t, J=7.4 Hz, 2H), 5.73 (d, J=7.6 Hz, 1H), 4.52 (dt, J=7.5, 4.8 Hz, 1H), 4.46-4.28 (m, 2H), 4.22 (m, 3H), 3.04 (m, 2H), 2.77 (t, J=6.6 Hz, 2H), 2.32-2.20 (m, 2H), 1.58 (d, J=6.8 Hz, 2H), 1.45 (d, J=26.7 Hz, 9H), 1.21 (m, 24H), 0.94-0.78 (t, 3H).
$^{13}$C NMR (101 MHz, CDCl$_3$) δ 173.61, 169.61, 155.75, 143.83, 141.33, 127.76, 127, 125.17, 120.02, 82.99, 67.18, 63.13, 54.38, 47.16, 34.92, 34.20, 31.99, 31.43, 29.76, 29.73, 29.68, 29.54, 29.44, 29.34, 29.20, 28.03, 24.94, 22.77, 14.22

N-Fluorenylmethoxycarbonyl-S-[2 Palmitoyloxy Ethyl]-(R)-cysteine (14)

Compound 13 (0.47 mmol, 0.32 g) was dissolved in neat TFA (5 mL) and stirred for 1 hour at RT. TLC analysis (10% EtOAc in PE, R$_f$=0.3) showed complete conversion. The reaction mixture was concentrated and co-evaporated with toluene in vacuo. The crude was adsorbed on Celite and purified by silica gel column chromatography (15:85 EA:Pnt+1% acetic acid, R$_f$=0.15). Compound 10 (0.42 mmol, 0.26 g) was obtained with a 90% yield.

$[α]_D$: +12.4°
IR (cm$^{-1}$)=3317, 2500-3200, 2916, 2848, 1732, 1691, 1537
HRMS [M+H]$^+$: 626.36067 (measured), 626.35099 (calculated).
$^1$H NMR (400 MHz, CDCl$_3$) δ 8.35 (s, 1H, COOH), 7.75 (d, J=7.5 Hz, 2H, C—H Fmoc), 7.60 (d, J=6.2 Hz, 2H C—H Fmoc), 7.39 (t, J=7.4 Hz, 2H C—H Fmoc), 7.30 (t, J=7.4 Hz, 2H C—H Fmoc), 5.79 (d, J=7.8 Hz, 1H, N$_{25}$), 4.66 (m, 1H, C$_2$), 4.50-4.33 (m, 2H, C$_{23}$), 4.31-4.08 (m, 3H, C$_{5+24}$), 3.09 (m, 2H, C$_3$), 2.77 (t, J=6.4 Hz, 2H, C$_4$), 2.28 (t, J=7.6 Hz, 2H, C$_7$), 1.57 (m, 2H, C$_8$), 1.24 (m, 24H, C$_{9-20}$), 0.88 (t, J=6.8 Hz, 3H, C$_{21}$).
$^{13}$C NMR (101 MHz, CDCl$_3$) δ 174.61 (C$_{1, 6}$), 174.11 (C$_{1, 6}$), 156.11 (C$_{22}$), 143.72 (C$_q$ Fmoc), 141.40 (C$_q$ Fmoc), 127.87 (C—H Fmoc), 127.20 (C—H Fmoc), 125.21 (C—H Fmoc), 120.12 (C—H Fmoc), 67.51 (C$_{23}$), 63.23 (C$_5$), 53.73 (C$_2$), 47.17 (C$_{24}$), 34.48 (C$_3$), 34.29 (C$_7$), 32.05, 31.35 (C$_4$), 29.83 (C$_{9-19}$), 29.79 (C$_{9-19}$), 29.75 (C$_{9-19}$), 29.61 (C$_{9-19}$), 29.49 (C$_{9-19}$), 29.40 (C$_{9-19}$), 29.26 (C$_{9-19}$), 24.99 (C$_8$), 22.82 (C$_{20}$), 14.27 (C$_{21}$).

HO—(CH$_2$CH$_2$O)$_3$CH$_2$C(O)OtBu (15)

Triethyleneglycol (40 mmol, 5.3 mL) was dissolved in dry THF (200 mL) under argon atmosphere. Sodium hydride (0.84 g, 21 mmol) was added at 0° C. Tetrabutylammonium iodide (2.0 mmol, 0.37 g) was added. Tert-butyl bromoacetate (20 mmol, 3.0 mL) was added and the reaction was stirred overnight at RT under argon atmosphere. The reaction mixture was filtrated and the THF was evaporated. The crude was adsorbed on Celite and purified by silica gel column chromatography (8:2 EA:Pnt). Compound 15 (7.7 mmol, 2.0 g) was obtained with a 40% yield.

IR (cm$^{-1}$)=2873 (C—H, stretch), 1742 (C=O, stretch).
HRMS [M+H]$^+$: 265.16298 (measured), 265.16456 (calculated).
$^1$H NMR (400 MHz, CDCl$_3$) δ 4.02 (s, 2H), 3.78-3.66 (m, 10H), 3.61 (dd, J=5.3, 3.8 Hz, 2H), 1.48 (s, 9H).
$^{13}$C NMR (101 MHz, CDCl$_3$) δ 169.67, 81.72 (C$_{10}$), 72.66, 70.62, 70.60, 70.49, 70.23, 68.97, 61.65, 28.10.

MsO—(CH$_2$CH$_2$O)$_3$CH$_2$C(O)OtBu (16)

Compound 15 (4.73 mmol, 1.25 g) was dissolved in DCM (50 mL). TEA (9.46 mmol, 1.30 mL) was added and the mixture was cooled to 0° C. MsCl (5.31 mmol, 0.41 mL) was slowly added. The mixture was heated to RT and stirred for 3 hours. TLC analysis (EA) indicated complete conversion. The reaction mixture was diluted with DCM and washed with 10% KHSO$_4$(aq) (3×), 10% NaHCO$_3$(aq) (3×) and brine (1×). The solution was dried (Na$_2$SO$_4$), filtrated and evaporated in vacuo. The crude was purified by silica gel column chromatography (5:5 EA:Pnt→8:2 EA:Pnt, Δ=10%). Compound 16 (4.25 mmol, 1.45 g) was obtained with a 90% yield.

IR (cm$^{-1}$)=2872 (C—H, stretch), 1742 (C=O, stretch).
HRMS [M+H]$^+$: 343.14186 (measured), 343.14211 (calculated).
$^1$H NMR (400 MHz, CDCl$_3$) δ 4.01 (s, 2H), 3.80-3.76 (m, 2H), 3.73-3.65 (m, 8H), 3.09 (s, 3H), 1.48 (s, 9H).
$^{13}$C NMR (101 MHz, CDCl$_3$) δ 169.58, 81.61, 70.68, 70.60, 70.53, 70.52, 69.37, 69.01, 68.96, 37.70, 28.11.

N$_3$—(CH$_2$CH$_2$O)$_3$CH$_2$C(O)OtBu (17)

Compound 16 (2.96 mmol, 1.01 g) was dissolved in DMF (30 mL). Sodium azide (9 mmol, 585 mg) was added and the mixture was heated to 60° C. After 4 hours of stirring TLC analysis (8:2 EA:Pnt) showed complete conversion. The mixture was diluted with EA and washed with 5% NaHCO$_3$ (aq) (4×). The solution was dried (Na$_2$SO$_4$), filtrated and evaporated in vacuo. The crude was purified by silica gel column chromatography (4:6 EA:Pnt→8:2 EA:Pnt, Δ=10%). Compound 17 (2.65 mmol, 766 mg) was obtained with a 90% yield.

IR (cm$^{-1}$)=2869 (C—H, stretch), 2099 (N=N=N, stretch), 1745 (C=O, stretch). HRMS [M+Na]$^+$: 312.15314 (measured), 312.15299 (calculated).
$^1$H NMR (400 MHz, CDCl$_3$) δ 4.03 (s, 2H), 3.76-3.65 (m, 10H), 3.44-3.35 (m, 2H), 1.48 (s, 9H).
$^{13}$C NMR (101 MHz, CDCl$_3$) δ 169.56, 81.42, 70.61, 70.58, 70.56, 70.54, 69.94, 68.92, 50.58, 28.01.

NH$_2$—(CH$_2$CH$_2$O)$_3$CH$_2$C(O)OtBu (18)

Compound 17 (2.22 mmol, 642 mg) was dissolved in dry THF (25 mL) under argon atmosphere. Triphenylphosphine (2.7 mmol, 707 mg) was added and the mixture was stirred for 20 hours. TLC analysis (6:4 Pnt:EA) indicated complete conversion. Water was added until white crystals were formed in the solution. The mixture was diluted with DCM and washed with 10% NaHCO$_3$(aq) (3×). The solution was dried (Na$_2$SO$_4$), filtrated and evaporated in vacuo. The crude was absorbed on Celite and purified by silica gel column chromatography (1% MeOH in DCM+1% TEA→10% MeOH in DCM+1% TEA, Δ=2.5%). Compound 18 (1 mmol, 264 mg) was obtained with a 45% yield.

IR (cm$^{-1}$)=3400 (N—H, stretch), 2874 (C—H, stretch), 1742 (C=O, stretch).

HRMS [M+H]$^+$: 264.18073 (measured), 264.18055 (calculated).

$^1$H NMR (400 MHz, CDCl$_3$) δ 5.40 (t, J=5.5 Hz, 1H), 4.04 (s, 2H), 3.71 (m, 4H), 3.63 (s, 4H), 3.55 (t, J=5.2 Hz, 2H), 3.37 (m, 2H), 1.48 (s, 9H).

$^{13}$C NMR (101 MHz, CDCl$_3$) δ 169.79, 81.84, 70.80, 70.76, 70.51, 70.48, 70.17, 69.06, 40.19, 28.22

FmocNH-Cys(EtOC(O)C$_{15}$H$_{31}$)-Ser(tBu)-OMe (19)

Compound 14 (1.27 mmol, 794 mg) was dissolved in dry DMF (10 mL). H-Ser(OtBu)-OMe·HCl (1.52 mmol, 321 mg) was added. A solution of TEA (1.91 mmol, 0.26 mL) in DMF (10 mL) was slowly added to the reaction mixture. HOBt (1.91 mmol, 258 mg) and DIC (1.9 mmol, 0.30 mL) were added and the mixture was stirred at RT for 2 hours under argon atmosphere. TLC analysis (3:7 EA:Pnt, R$_f$=0.2, ninhydrine) showed complete conversion. The crude was dissolved in DCM and washed with H$_2$O. The solution was dried (MgSO$_4$), filtrated, concentrated and co-evaporated with toluene in vacuo. The crude was adsorbed on Celite and purified by silica gel column chromatography (2:8 EA:Pnt, R$_f$=0.15). 19 (1.12 mmol, 873 mg) was obtained with a 88% yield.

[α]$_D$: +8°

IR (cm$^{-1}$)=3298, 2918, 2848, 1734, 1660, 1531

HRMS [M+H]$^+$: 783.46038 (measured), 783.46126 (calculated).

$^1$H NMR (400 MHz, CDCl$_3$) δ 7.74 (d, J=7.5 Hz, 2H), 7.59 (d, J=7.4 Hz, 2H), 7.38 (t, J=7.5 Hz, 2H), 7.29 (t, J=7.4 Hz, 3H), 5.99 (d, J=7.1 Hz, 1H), 4.69 (dd, J=5.1, 3.1 Hz, 1H), 4.54-4.30 (m, 3H), 4.23 (m, 3H), 3.82 (dd, J=9.1, 2.7 Hz, 1H), 3.72 (s, 3H), 3.57 (dd, J=9.1, 3.0 Hz, 1H), 2.98 (d, J=3.9 Hz), 2.84 (s, 2H), 2.29 (t, J=7.6 Hz, 2H), 1.59 (dd, J=14.0, 7.0 Hz, 2H), 1.26 (m, 24H), 1.12 (s, 9H), 0.88 (t, J=6.8 Hz, 3H).

$^{13}$C NMR (101 MHz, CDCl$_3$) δ 173.66, 170.43, 170.14, 155.91, 143.76, 141.26, 127.72, 127.07, 125.15, 119.97, 73.56, 67.27, 62.92, 61.62, 54.14, 53.21, 52.43, 47.08, 34.91, 34.16, 31.93, 30.99, 29.70, 29.66, 29.62, 29.48, 29.37, 29.29, 29.15, 27.26, 24.88, 22.70, 14.15.

NH$_2$-Cys(EtOC(O)C$_{15}$H$_{31}$)-Ser(tBu)-OMe (20)

19 (0.50 mmol, 0.39 g) was dissolved in dry DMF (10 mL). A solution of 2% piperidine and 2% DBU in DMF (10 mL) was slowly added. The mixture was stirred for 15 min at RT under argon atmosphere. TLC analysis (95:5 DCM:MeOH, R$_f$=0.8, ninhydrine) showed complete conversion. The mixture was taken up in EA and washed with 10% KHSO$_4$(aq) (2×) and H$_2$O (2×). The solution was dried (MgSO$_4$), filtrated, concentrated and co-evaporated with toluene in vacuo. The crude was adsorbed on Celite and purified by silica gel column chromatography (99% DCM, 1% MeOH+0.1% TEA, R$_f$=0.1). Compound 20 (0.44 mmol, 0.25 g) was obtained with an 88% yield.

[α]$_D$: −49.2°

IR (cm$^{-1}$)=3178, 3082, 2917, 2851, 1744, 1677, 1660, 1464

HRMS [M+H]$^+$: 561.39046 (measured), 561.39318 (calculated).

$^1$H NMR (400 MHz, CDCl$_3$) δ 8.06 (d, J=8.5 Hz, 1H), 4.67 (dt, J=8.6, 3.2 Hz, 1H), 4.22 (t, J=6.7 Hz, 2H), 3.83 (dd, J=9.1, 3.2 Hz, 1H), 3.75 (s, 3H), 3.56 (m, 2H), 3.09 (dd, J=13.6, 3.8 Hz, 1H), 2.83-2.74 (m, 3H), 2.32 (t, J=7.6 Hz, 2H), 1.62 (m, 2H), 1.27 (s, 24H), 1.15 (s, 9H), 0.88 (t, J=6.8 Hz, 3H).

$^{13}$C NMR (101 MHz, CDCl$_3$) δ 173.68, 173.26, 170.92, 73.47, 63.12, 62.06, 54.19, 52.76, 52.41, 37.93, 34.25, 32.00, 30.68, 29.76, 29.73, 29.68, 29.54, 29.43, 29.35, 29.21, 27.39, 24.98, 22.77, 14.20.

AcNH-Cys(EtOC(O)C$_{15}$H$_{31}$)-Ser(tBu)-OMe

Compound 20 (0.17 mmol, 95 mg) was dissolved in dry DCM (2 mL). A solution of TEA (0.25 mmol, 36 μL) in dry DCM (1 mL) was slowly added. Acetic anhydride (0.34 mmol, 32 μL) was added and the mixture was stirred overnight at RT under argon atmosphere. TLC analysis (93:7 DCM:MeOH, R$_f$=0.3, ninhydrine) showed complete conversion. The mixture was taken up in DCM and washed with a saturated solution of NH$_4$Cl (aq). The solution was dried (MgSO$_4$), filtrated and concentrated in vacuo. The crude was dissolved in DCM and purified by silica gel column chromatography (99:1 DCM:MeOH, R$_f$=0.15, ninhydrine). AcNH-Cys(EtOC(O)C$_{15}$H$_{31}$)—Ser(tBu)-OMe (0.16 mmol, 96 mg) was obtained with a 94% yield.

[α]$_D$: +17.8°

IR (cm$^{-1}$)=3285, 2916, 2849, 1737, 1660

HRMS [M+H]$^+$: 603.40167 (measured), 603.40375 (calculated).

$^1$H NMR (400 MHz, CDCl$_3$) δ 7.29 (d, J=8.2 Hz, 1H), 6.77 (d, J=7.4 Hz, 1H), 4.72-4.60 (m, 2H), 4.26 (t, J=6.6 Hz, 2H), 3.83 (dd, J=9.1, 3.0 Hz, 1H), 3.75 (s, 3H), 3.57 (dd, J=9.1, 3.3 Hz, 1H), 3.03-2.80 (m, 4H), 2.32 (t, J=7.6 Hz, 2H), 2.04 (s, 3H), 1.61 (m, 2H), 1.35-1.20 (m, 24H), 1.14 (s, 9H), 0.88 (t, J=6.8 Hz, 3H).

$^{13}$C NMR (101 MHz, CDCl$_3$) δ 173.71, 170.44, 170.34, 170.02, 73.57, 62.83, 61.54, 53.24, 52.46, 52.44, 34.59, 34.22, 31.95, 30.97, 29.72, 29.68, 29.64, 29.50, 29.39, 29.31, 29.18, 27.29, 24.91, 23.11, 22.72, 14.16.

C$_{15}$H$_{31}$C(O)NH-Cys(EtOC(O)C$_{15}$H$_{31}$)—Ser(tBu)-OMe

Compound 20 (0.17 mmol, 95 mg) was dissolved in dry pyridine (2 mL). Palmitoyl chloride (0.21 mmol, 63 μL) was added and the mixture was stirred at RT under argon atmosphere for 45 min. TLC analysis (93:7 DCM:MeOH, R$_f$=0.3, ninhydrine) showed complete conversion. The reaction mixture was taken up in DCM and washed with 10% KHSO$_4$(aq). The solution was dried (MgSO$_4$), filtrated and concentrated in vacuo. The crude was dissolved in DCM and purified by silica gel column chromatography (99.5:0.5 DCM:MeOH 99:1 DCM:MeOH, R$_f$=0.1). C$_{15}$H$_{31}$C(O)NH-Cys(EtOC(O)C$_{15}$H$_{31}$)-Ser(tBu)-OMe (0.17 mmol, 0.13 g) was obtained with a quantitative yield.

[α]$_D$: +10.6°

IR (cm$^{-1}$)=3283, 2915, 2848, 1737, 1639

HRMS [M+H]$^+$: 799.62276 (measured), 799.62285 (calculated).

$^1$H NMR (400 MHz, CDCl$_3$) δ 7.32 (d, J=8.2 Hz, 1H), 6.74 (d, J=7.4 Hz, 1H), 4.71-4.62 (m, 2H), 4.26 (t, J=6.6 Hz,

2H), 3.83 (dd, J=9.1, 3.0 Hz, 1H), 3.74 (s, 3H), 3.57 (dd, J=9.1, 3.3 Hz, 1H), 3.00-2.82 (m, 4H), 2.32 (m, 2H), 2.28-2.20 (m, 2H), 1.69-1.56 (m, 4H), 1.37-1.20 (m, 48H), 1.14 (s, 9H), 0.88 (t, J=6.8 Hz, 6H).

$^{13}$C NMR (101 MHz, CDCl$_3$) δ 173.64, 173.20, 170.51, 170.34, 73.54, 62.84, 61.47, 53.23, 52.40, 52.22, 36.46, 34.57, 34.17, 33.97, 31.91, 30.90, 29.69, 29.65, 29.63, 29.49, 29.47, 29.35, 29.28, 29.26, 29.15, 27.23, 25.57, 24.87, 22.68, 14.10.

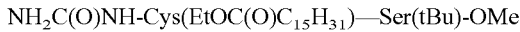

NH$_2$C(O)NH-Cys(EtOC(O)C$_{15}$H$_{31}$)—Ser(tBu)-OMe

Compound 20 (0.39 mmol, 0.22 g) was dissolved in dry DCM (10 mL). Isopropanol (8.0 mmol, 0.61 mL) was added. 85% (Trimethylsilyl)isocyanate (4.0 mmol, 0.65 mL) was added and the mixture was stirred overnight at RT under argon atmosphere. TLC analysis (1:1 EA:Pnt+1% TEA) indicated completion of reaction. Celite was added to the reaction mixture and the DCM was evaporated in vacuo. The adsorbed crude was purified by silica gel column chromatography (1:1 EA:Pnt+1% TEA→95:5 EA:MeOH+1% TEA). NH$_2$C(O)NH-Cys(EtOC(O)C$_{15}$H$_{31}$)-Ser(tBu)-OMe (0.40 mmol, 0.24 g) was obtained with a quantitative yield.

[α]$_D$: +10.3°
IR (cm$^{-1}$)=2916, 2849, 1733, 1645,
HRMS [M+H]$^+$: 604.39816 (measured), 604.39900 (calculated).

$^1$H NMR (400 MHz, CDCl$_3$) δ 7.47 (d, J=8.1 Hz, 1H), 6.46 (d, J=7.9 Hz, 1H), 5.15 (m, 1H), 4.69-4.54 (m, 2H), 4.31-4.18 (m, 2H), 3.80 (dd, J=9.1, 3.3 Hz, 1H), 3.74 (s, 3H), 3.58 (dd, J=9.2, 3.5 Hz, 1H), 2.94 (m, 2H), 2.83 (m, 2H), 2.31 (t, J=7.6 Hz, 2H), 1.60 (m, 2H), 1.35-1.20 (m, 24H), 1.14 (s, 9H), 0.88 (t, J=6.8 Hz, 3H).

$^{13}$C NMR (101 MHz, CDCl$_3$) δ 173.99, 171.66, 170.62, 158.57, 73.70, 63.01, 61.68, 53.44, 53.33, 52.51, 35.35, 34.29, 32.00, 31.13, 29.77, 29.74, 29.57, 29.44, 29.38, 29.25, 27.34, 24.97, 22.76, 14.20

AcNH-Cys(EtOC(O)C$_{15}$H$_{31}$)-Ser(OH)—OMe (1)

AcNH-Cys(EtOC(O)C$_{15}$H$_{31}$)-Ser(tBu)-OMe (0.24 mmol, 145 mg) was dissolved in TFA (5 mL) and was stirred at RT. After 30 min the mixture was dropped in Et$_2$O and precipitated overnight at −20° C. Compound 1 (0.15 mmol, 82 mg) was obtained with a 62% yield.

[α]$_D$: +7.0°
IR (cm$^{-1}$)=3281, 2914, 2849, 1737, 1630,
HRMS [M+H]$^+$: 547.33966 (measured), 547.34115 (calculated).

$^1$H NMR (400 MHz, CDCl$_3$) δ 7.64 (d, J=7.9 Hz, 1H), 6.91 (d, J=7.5 Hz, 1H), 4.71 (dd, J=13.7, 6.8 Hz, 1H), 4.67-4.61 (m, 1H), 4.33-4.16 (m, 2H), 3.94 (ddd, J=25.2, 11.6, 3.5 Hz, 2H), 3.78 (s, 3H), 2.96 (qd, J=13.9, 6.5 Hz, 2H), 2.81 (t, J=6.7 Hz, 2H), 2.32 (t, J=7.6 Hz, 2H), 2.05 (s, 3H), 1.68-1.54 (m, 2H), 1.36-1.19 (m, 24H), 0.88 (t, J=6.8 Hz, 3H).

$^{13}$C NMR (101 MHz, CDCl$_3$) δ 174.17, 171.31, 170.71, 170.64, 62.88, 62.61, 55.12, 52.85, 34.56, 34.34, 32.04, 31.14, 29.81, 29.78, 29.74, 29.61, 29.48, 29.40, 29.27, 25.00, 23.10, 22.81, 14.24.

C$_{15}$H$_{31}$C(O)NH-Cys(EtOC(O)C$_{15}$H$_{31}$)-Ser(OH)—OMe (2)

C$_{15}$H$_{31}$C(O)NH-Cys(EtOC(O)C$_{15}$H$_{31}$)—Ser(tBu)-OMe (0.31 mmol, 245 mg) was dissolved in TFA (5 mL) and was stirred at RT. After 30 min the mixture was dropped in Et$_2$O and precipitated over weekend at −20° C. Compound 2 (0.29 mmol, 217 mg) was obtained with a 94% yield.

[α]$_D$: +2.9°
IR (cm$^{-1}$)=3313, 2910, 2848, 1739, 1639
HRMS [M+H]$^+$: 743.56003 (measured), 743.56025 (calculated).

$^1$H NMR (400 MHz, CDCl$_3$) δ 7.61 (d, J=7.7 Hz, 1H), 6.87 (d, J=7.3 Hz, 1H), 4.77-4.58 (m, 2H), 4.36-4.15 (m, 2H), 3.96 (m, 2H), 3.80 (d, J=10.2 Hz, 3H), 3.05-2.89 (m, 2H), 2.82 (t, J=6.6 Hz, 2H), 2.29 (m, 4H), 1.61 (m, 4H), 1.37-1.16 (m, 48H), 0.88 (t, J=6.6 Hz, 6H).

$^{13}$C NMR (101 MHz, CDCl$_3$) δ 174.95, 174.34, 170.83, 170.50, 62.88, 62.61, 55.14, 52.91, 52.77, 36.47, 34.43, 34.36, 32.05, 31.15, 29.83, 29.79, 29.63, 29.49, 29.42, 29.36, 29.28, 25.75, 25.00, 22.82, 14.24.

NH$_2$C(O)NH-Cys(EtOC(O)C$_{15}$H$_{31}$)-Ser(OH)—OMe (3)

NH$_2$C(O)NH-Cys(EtOC(O)C$_{15}$H$_{31}$)—Ser(tBu)-OMe (0.37 mmol, 225 mg) was dissolved in TFA (5 mL) and was stirred at RT. After 30 min the mixture was co-evaporated with toluene in vacuo. After silica gel column chromatography purification (1% MeOH in EA→4% MeOH in EA) compound 3 (0.33 mmol, 180 mg) was obtained with a 89% yield.

[α]$_D$: +3.3°
IR (cm$^{-1}$)=3286, 2916, 2849, 1742, 1639
HRMS [M+H]$^+$: 548.33519 (measured), 548.33640 (calculated).

$^1$H NMR (400 MHz, DMSO) δ 8.37 (d, J=7.8 Hz, 1H), 6.25 (d, J=8.7 Hz, 1H), 5.68 (s, 2H), 5.08 (t, J=5.6 Hz, 1H), 4.49-4.39 (m, 1H), 4.36 (m, 1H), 4.21-4.06 (m, 2H), 3.71 (m, 1H), 3.67-3.56 (m, 4H), 2.83 (dd, J=13.7, 5.2 Hz, 1H), 2.75 (m, 2H), 2.65 (dd, J=13.7, 7.7 Hz, 1H), 2.28 (t, J=7.4 Hz, 2H), 1.59-1.45 (m, 2H), 1.33-1.15 (m, 24H), 0.85 (t, J=6.8 Hz, 3H).

$^{13}$C NMR (101 MHz, DMSO) δ 172.76, 171.34, 170.74, 157.95, 62.88, 61.17, 54.61, 52.25, 51.84, 34.89, 33.40, 31.29, 29.99, 29.04, 28.88, 28.70, 28.44, 24.42, 22.09, 13.96

AcNH-Cys(EtOC(O)C$_{15}$H$_{31}$)-SerLysLysLysLys-C(O)NH$_2$ (4)

The SK$_4$ peptide was prepared by applying Fmoc based protocol starting from Tentagel S RAM resin (4.35 g; loading 0.23 mmol/g) on a AB peptide synthesizer. The amino acids used were Fmoc-Lys(Boc) and Fmoc-Ser(OtBu)-OH. To a mixture of resin bound peptide (SK$_4$) (0.05 mmol; 0.228 g) in NMP/DCM (1:1) was added 14 (0.125 mmol; 0.78 g), PyBop (0.175 mmol; 0.091 g) and DiPEA 1M (0.25 mmol; 0.032 g; 250 μL). The DiPEA was added in two times, first an amount of 125 μL, after 10 min another amount of 125 μL. The reaction mixture was then stirred overnight on the orbital shaker at rt. The resin was washed three times with DCM and the Fmoc was cleaved with 20% piperidine/DMF (3 times 5 min). The now free amine acetylated by adding acetyl chloride (0.5 mmol; 0.039 g; 35 μL) in pyridine/DCM (1:1), the mixture was stirred for 2.5 h. The solution was washed with DCM three times and the resulting conjugate was cleaved off the resin by adding TFA/TiS/H2O (95/2.5/2.5) (2 h). Purification of the conjugate was done by adding the crude to cold diethylether/n-pentane (1:1) (14 mL) and centrifugation (4000 rpm, 5 min) was performed. The precipitate was dissolved in magic (MeCN/t-BuOH/H$_2$O) (1:3:1). This solution was then subjected to semi-prep HPLC, pure lipopeptide fractions were collected and concentrated by freeze-drying. This yielded conjugate 4 (5.6 µmol; 5.8 mg; 7.7%). LCMS: 10-90% c18, Rt=6.4 min;

NH$_2$C(O)NH-Cys(EtOC(O)C$_{15}$H$_{31}$)—SerLysLys-LysLys-C(O)NH$_2$ (5)

To synthesize 5, the coupling of building block 14 to the pentapeptide SK$_4$ was done under the same conditions described by the coupling procedure for compound 4. After the coupling, DCM wash and the cleavage of the Fmoc, the free amine was treated with TMS-isocyanate (0.5 mmol; 0.058 gr; 68 µL) and isopropanol (1 mmol; 0.06 g; 76 µL) in DCM. Further procedure and purification was done according to the same method explained for compound 4. This provided compound 5 (2.9 µmol; 3.0 mg; 4%). LCMS: 10-90% c18, Rt=6.3 min.

FmocNH-Ser(OtBu)-O(CH$_2$CH$_2$O)$_3$CH$_2$C(O)OtBu

Compound 15 (2.8 mmol, 1.6 g) was dissolved in dry DCM (30 mL). Fmoc-Ser(OtBu)-OH (3.38 mmol, 1.29 g), DIC (3.36 mmol, 0.52 mL) and DMAP (0.3 mmol, 38 mg) were added and the mixture was stirred for 4 hours at RT under argon atmosphere. TLC-MS indicated complete conversion. The reaction mixture was diluted with DCM and washed with 10% KHSO$_4$(aq)(3×), 10% NaHCO$_3$(aq)(3×) and brine (1×). The solution was dried (Na$_2$SO$_4$), filtrated and evaporated in vacuo. The crude was dissolved in THF and the urea byproduct was removed by crystallization at −20° C. The crude was further purified by silica gel column chromatography (8:2 Pnt:EA→7:3 Pnt:EA, R$_f$=0.3). Product (1.74 g, 2.77 mmol) was obtained with a quantitative yield.

[α]$_D$: +6.33°
IR (cm$^{-1}$)=2974, 2873, 1738, 1722, 1717
HRMS [M+H]$^+$: 630.32709 (measured), 630.32727 (calculated).
$^1$H NMR (400 MHz, CDCl$_3$) δ 7.76 (d, J=7.5 Hz, 2H), 7.63 (t, J=7.1 Hz, 2H), 7.40 (t, 2H), 7.31 (t, 2H), 5.75 (d, J=8.9 Hz, 1H), 4.56-4.49 (m, 1H), 4.48-4.07 (m, 5H), 4.01 (s, 2H), 3.86 (dd, J=9.0, 2.8 Hz, 1H), 3.76-3.54 (m, 11H), 1.47 (s, 9H), 1.16 (s, 9H).
$^{13}$C NMR (101 MHz, CDCl$_3$) δ 170.62, 169.64, 156.11, 143.99, 143.81, 141.27, 127.70, 127.08, 125.21, 125.17, 119.97, 81.55, 73.47, 70.69, 70.62, 70.57, 69.00, 68.98, 67.16, 64.54, 62.11, 54.67, 47.14, 28.12, 27.35

NH$_2$-Ser(OtBu)-O(CH$_2$CH$_2$O)$_3$CH$_2$C(O)OtBu (21)

FmocNH-Ser(OtBu)-O(CH$_2$CH$_2$O)$_3$CH$_2$C(O)OtBu (1.629 g, 2.59 mmol) was dissolved in dry DMF (10 mL). A mixture of 2:2 piperidine and DBU (v:v) in dry DMF (30 mL) was added. The mixture was stirred for 15 minutes at RT under argon atmosphere. TLC (6:4 Pnt:EA) indicated complete conversion. The reaction mixture was diluted with EA and washed with 0.25% KHSO$_4$(aq) (3×), 10% NaHCO$_3$ (aq) (3×) and brine (1×). The solution was dried (Na$_2$SO$_4$), filtrated and evaporated in vacuo. The crude was adsorbed on Celite and purified with silica gel column chromatography (DCM→95:5 DCM:MeOH, Δ=0.5%). Compound 21 (1.97 mmol, 802 mg) was obtained with a 76% yield.

[α]$_D$: −8.95°
IR (cm$^{-1}$)=2974, 2872, 1742
HRMS [M+H]$^+$: 408.25702 (measured), 408.25919 (calculated).
$^1$H NMR (400 MHz, CDCl$_3$) δ 4.29 (m, 2H), 4.02 (s, 2H), 3.76-3.51 (m, 13H), 1.48 (s, 9H), 1.09 (s, 9H).

$^{13}$C NMR (101 MHz, CDCl$_3$) δ 174.22, 169.74, 81.72, 73.23, 70.81, 70.72, 70.65, 70.33, 69.12, 69.09, 64.12, 63.83, 55.26, 28.22, 27.57.

FmocNH-Cys(EtOC(O)C$_{15}$H$_{31}$)—Ser(OtBu)-O(CH$_2$CH$_2$O)$_3$CH$_2$C(O)OtBu 21 (0.70 mmol, 0.29 g) was dissolved in dry DMF (5 mL). Compound 14 (0.50 mmol, 0.31 g), HOBt (0.70 mmol, 94 mg) and DIC (0.70 mmol, 0.11 mL) was added. The mixture was stirred overnight at RT under argon atmosphere. TLC-MS indicated complete conversion. The mixture was diluted with EA and washed with 10% NaHCO$_3$(aq) (2×), 10% KHSO$_4$(aq) (2×) and brine (1×). The solution was dried (Na$_2$SO$_4$), filtrated and evaporated in vacuo. The crude was dissolved in THF and the urea byproduct was removed by crystallization at −20° C. The crude was adsorbed on Celite and purified by silica gel column chromatography (8:2 Pnt:EA→5:5 Pnt:EA, Δ=10%). Product (0.35 mmol, 0.36 g) was obtained with a 71% yield.

[α]$_D$: +4.83°
IR (cm$^{-1}$)=2923, 2852, 1733, 1739
HRMS [M+H]$^+$: 1015.59320 (measured), 1015.59234 (calculated).
$^1$H NMR (400 MHz, CDCl$_3$) δ 7.76 (d, J=7.5 Hz, 2H), 7.60 (d, J=7.4 Hz, 2H), 7.40 (t, J=7.4 Hz, 2H), 7.30 (m, 3H), 5.88 (d, J=6.5 Hz, 1H), 4.70 (dt, J=8.2, 3.0 Hz, 1H), 4.48-4.34 (m, 3H), 4.32-4.17 (m, 5H), 4.01 (s, 2H), 3.86 (dd, J=9.1, 2.9 Hz, 1H), 3.75-3.65 (m, 10H), 3.59 (dd, J=9.1, 3.1 Hz, 1H), 2.98 (s, 2H), 2.86 (s, 2H), 2.30 (t, J=7.6 Hz, 2H), 1.59 (m, 2H), 1.47 (s, 9H), 1.27 (d, J=22.4 Hz, 24H), 1.13 (s, 9H), 0.88 (t, J=6.8 Hz, 3H). $^{13}$C NMR (101 MHz, CDCl$_3$) δ 173.79, 170.01, 169.75, 143.85, 141.41, 127.85, 127.21, 125.27, 125.22, 81.71, 73.69, 70.83, 70.73, 70.69, 70.66, 69.13, 69.06, 67.38, 64.70, 63.02, 61.72, 54.25, 53.37, 47.23, 35.06, 34.31, 32.05, 31.13, 29.82, 29.78, 29.75, 29.60, 29.48, 29.42, 29.29, 28.24, 27.44, 25.01, 22.82, 14.25.

NH$_2$-Cys(EtOC(O)C$_{15}$H$_{31}$)-Ser(OtBu)-O(CH$_2$CH$_2$O)$_3$CH$_2$C(O)OtBu (23)

FmocNH-Cys(EtOC(O)C$_{15}$H$_{31}$)-Ser(OtBu)-O(CH$_2$CH$_2$O)$_3$CH$_2$C(O)OtBu (0.29 mmol, 0.29 g) was dissolved in dry DCM (5 mL). Octanethiol (1.5 mmol, 0.25 mL), then DBU (0.03 mmol, 5 µL) was added and the mixture was stirred overnight at RT. TLC (8:2 EA:Pnt) indicated complete conversion. Celite was added to the reaction mixture and the DCM was evaporated in vacuo. The adsorbed crude was purified by silica gel column chromatography (EA+1% TEA→9:1 EA:MeOH+1% TEA). Compound 23 (0.26 mmol, 203 mg) was obtained with a 90% yield.

[α]$_D$: −41.42°
IR (cm$^{-1}$)=2918, 2850, 1742, 1677, 1662,
HRMS [M+H]$^+$: 793.52330 (measured), 793.52426 (calculated).
$^1$H NMR (400 MHz, CDCl$_3$) δ 8.07 (d, J=8.6 Hz, 1H), 4.69 (dt, J=8.6, 3.2 Hz, 1H), 4.30 (t, 2H), 4.22 (t, J=6.7 Hz, 2H), 4.02 (d, J=2.5 Hz, 2H), 3.85 (dd, J=9.0, 3.1 Hz, 1H), 3.75-3.66 (m, 10H), 3.63-3.52 (m, 2H), 3.09 (dd, J=13.6, 3.8 Hz, 1H), 2.82-2.70 (m, 3H), 2.31 (t, J=7.5 Hz, 2H), 1.67-1.56 (m, 2H), 1.48 (s, 9H), 1.36-1.21 (m, 23H), 1.13 (d, J=9.3 Hz, 9H), 0.88 (t, J=6.8 Hz, 3H).
$^{13}$C NMR (101 MHz, CDCl$_3$) δ 173.61, 173.24, 170.35, 169.65, 81.55, 73.37, 72.58, 70.74, 70.66, 70.62, 70.35, 69.03, 64.51, 63.06, 62.02, 54.16, 52.72, 37.88, 34.21,

NH$_2$C(O)NH-Cys(EtOC(O)C$_{15}$H$_{31}$)-Ser(OtBu)-O(CH$_2$CH$_2$O)$_3$CH$_2$C(O)OtBu

Compound 23 (0.23 mmol, 0.18 g) was dissolved in dry DCM (20 mL). Isopropanol (4.6 mmol, 0.35 mL) was added. 85% (Trimethylsilyl)isocyanate (2.3 mmol, 0.37 mL) was added and the mixture was stirred overnight at RT under argon atmosphere. TLC (EA, R$_f$=0.5, ninhydrine) indicated complete conversion. The mixture was diluted with DCM and washed with 10% NaHCO$_3$(aq) (2×), 10% KHSO$_4$(aq) (2×) and brine (1×). The solution was dried (Na$_2$SO$_4$), filtrated and evaporated in vacuo. The crude was adsorbed on Celite and purified by silica gel column chromatography (8:2 EA:Pnt+1% TEA). Product (0.21 mmol, 0.18 g) was obtained with a 90% yield.

[α]$_D$: +3°
IR (cm$^{-1}$)=2917, 2849, 1739, 1733, 1641,
HRMS [M+H]$^+$: 836.52912 (measured), 836.53007 (calculated).
$^1$H NMR (400 MHz, CDCl$_3$) δ 7.41 (d, J=8.2 Hz, 1H), 6.15 (d, J=7.6 Hz, 1H), 4.98 (s, 2H), 4.64 (dt, J=8.1, 3.3 Hz, 1H), 4.51 (dd, J=13.5, 6.4 Hz, 1H), 4.37-4.19 (m, 4H), 4.05-4.00 (m, 2H), 3.84 (dd, J=9.1, 3.3 Hz, 1H), 3.75-3.62 (m, 10H), 3.59 (dd, J=9.1, 3.4 Hz, 1H), 3.08-2.89 (m, 2H), 2.87-2.81 (m, 2H), 2.32 (t, 2H), 1.65-1.56 (m, 3H), 1.47 (s, 9H), 1.35-1.21 (m, 24H), 1.15 (s, 9H), 0.88 (t, J=6.9 Hz, 3H).
$^{13}$C NMR (101 MHz, CDCl$_3$) δ 174.03, 171.33, 170.11, 158.33, 73.66, 70.83, 70.68, 70.65, 70.60, 69.06, 64.71, 63.04, 61.71, 53.62, 53.45, 35.11, 34.35, 32.04, 31.14, 29.82, 29.78, 29.61, 29.48, 29.42, 29.29, 28.24, 27.45, 25.02, 22.81, 14.25.

NH$_2$C(O)NH-Cys(EtOC(O)C$_{15}$H$_{31}$)-Ser(OH)—O(CH$_2$CH$_2$O)$_3$CH$_2$C(O)OH (6)

NH$_2$C(O)NH-Cys(EtOC(O)C$_{15}$H$_{31}$)-Ser(OtBu)-O(CH$_2$CH$_2$O)$_3$CH$_2$C(O)OtBu (50 μmol, 42 mg) was dissolved in dry DCM (2 mL). TFA (2 mL) was added and the mixture was stirred for 1 hour at RT under argon atmosphere. LC-MS indicated complete conversion. The reaction mixture was dropped in a tube with Et$_2$O (9 mL) and left at −20° C. overnight. The tube was centrifuged and the precipitate was collected. Compound 6 (39 μmol, 28 mg) was obtained with an 80% yield.

[α]$_D$: −6.3°
IR (cm$^{-1}$)=3291, 2916 (C—H, stretch), 2849, 1739, 1641,
HRMS [M+H]$^+$: 724.40325 (measured), 724.40487 (calculated).
$^1$H NMR (400 MHz, CDCl$_3$) δ 8.06 (s, 1H), 6.53 (s, 1H), 4.67 (s, 2H), 4.43 (s, 1H), 4.37-4.07 (m, 5H), 3.95 (m, 2H), 3.69 (d, J=26.1 Hz, 10H), 2.97 (s, 2H), 2.79 (s, 2H), 2.31 (t, J=7.5 Hz, 2H), 1.59 (m, 2H), 1.25 (m, 24H), 0.88 (t, J=6.7 Hz, 3H).
$^{13}$C NMR (101 MHz, CDCl$_3$) δ 174.07, 70.49, 68.98, 63.17, 34.34, 32.06, 31.04, 29.85, 29.80, 29.66, 29.50, 29.33, 25.04, 22.83, 14.27.

FmocNH-Ser(OtBu)-NH(CH$_2$CH$_2$O)$_3$CH$_2$C(O)OtBu

Compound 18 (0.79 mmol, 0.17 g) was dissolved in dry DCM (30 mL). Fmoc-Ser(OtBu)-OH (1 mmol, 383 mg), DIC (1 mmol, 0.16 mL) and HOBt (1 mmol, 134 mg) were added and the mixture was stirred for 4 hours at RT under argon atmosphere. TLC-MS indicated complete conversion. The reaction mixture was diluted with DCM and washed with 10% KHSO$_4$(aq)(3×), 10% NaHCO$_3$(aq)(3×) and brine (1×). The solution was dried (Na$_2$SO$_4$), filtrated and evaporated in vacuo. The crude was adsorbed on Celite and purified by silica gel column chromatography (8:2 Pnt:EA→5:5 Pnt:EA, Δ=10%). Product (0.37 mmol, 235 mg) was obtained with a 47% yield. R$_f$=0.5 at 8:2 EA:Pnt.

[α]D: +15.8°
IR (cm$^{-1}$)=2974, 2868, 1723, 1717, 1668,
HRMS [M+H]$^+$: 629.34200 (measured), 629.34326 (calculated).
$^1$H NMR (400 MHz, CDCl$_3$) δ 7.76 (d, J=7.4 Hz, 2H), 7.61 (d, J=6.8 Hz, 2H), 7.40 (t, J=7.4 Hz, 2H), 7.31 (t, J=7.3 Hz, 2H), 7.09 (s, 1H), 5.85 (s, 1H), 4.39 (d, J=4.6 Hz, 2H), 4.23 (t, J=6.9 Hz, 2H), 4.00 (s, 2H), 3.84-3.73 (m, 1H), 3.73-3.53 (m, 10H), 3.53-3.44 (m, 2H), 3.40 (t, J=8.1 Hz, 1H), 1.46 (s, 9H), 1.20 (s, 9H). $^{13}$C NMR (101 MHz, CDCl$_3$) δ 170.38, 141.40, 127.83, 127.19, 125.26, 120.10, 70.77, 70.66, 70.62, 70.43, 69.93, 69.08, 62.07, 54.68, 47.28, 39.54, 28.23, 27.53

NH$_2$-Ser(OtBu)-NH(CH$_2$CH$_2$O)$_3$CH$_2$C(O)OtBu

FmocNH-Ser(OtBu)-NH(CH$_2$CH$_2$O)$_3$CH$_2$C(O)OtBu (0.16 mmol, 0.10 g) was dissolved in dry DCM (5 mL). Octanethiol (0.80 mmol, 0.14 mL) was added. DBU (0.02 mmol, 3 μL) was added and the mixture was stirred at RT overnight under argon atmosphere. TLC analysis (8:2 EA:Pnt) indicated completion of reaction. The DCM was evaporated in vacuo and the mixture was diluted with EA. The crude was purified by silica gel column chromatography (EA+1% TEA→9:1 EA:MeOH+1% TEA). Compound 22 (0.16 mmol, 65 mg) was obtained with a quantitative yield.

[α]$_D$: −9.1°
IR (cm$^{-1}$)=2973, 2930, 2872, 1746, 1661.
HRMS [M+H]$^+$: 407.27390 (measured), 407.27518 (calculated).
$^1$H NMR (400 MHz, CDCl$_3$) δ 7.74 (s, 1H), 4.02 (s, 2H), 3.74-3.54 (m, 11H), 3.47 (m, 4H), 1.48 (s, 9H), 1.19 (s, 9H).
$^{13}$C NMR (101 MHz, CDCl$_3$) δ 173.25, 169.68, 81.69, 73.40, 70.70, 70.59, 70.54, 70.29, 69.96, 69.01, 64.07, 55.52, 38.91, 28.14, 27.55.

FmocNH-Cys(EtOC(O)C$_{15}$H$_{31}$)-Ser(OtBu)-NH(CH$_2$CH$_2$O)$_3$CH$_2$C(O)OtBu 22 (0.28 mmol, 0.11 g) was dissolved in dry DCM (10 mL). Compound 14 (0.25 mmol, 156 mg), HOBt (0.30 mmol, 40 mg) and DIC (0.30 mmol, 50 μL) were added and the mixture was stirred overnight at RT under argon atmosphere. TLC analysis (EA) indicated completion of reaction. The reaction mixture was diluted with DCM and washed with 10% KHSO$_4$(aq) (3×), 10% NaHCO$_3$(aq) (3×) and brine (1×). The solution was dried (Na$_2$SO$_4$), filtrated and evaporated in vacuo. The crude was adsorbed on Celite and purified by silica gel column chromatography (8:2 Pnt:EA→EA). product (0.25 mmol, 0.25 g) was obtained with a quantitative yield. R$_f$=0.6 EA.

[α]$_D$: +7.3°
IR (cm$^{-1}$)=3300, 2920, 2820, 1736, 1733, 1641
HRMS [M+H]$^+$: 1014.60823 (measured), 1014.60832 (calculated).
$^1$H NMR (400 MHz, CDCl$_3$) δ 7.76 (d, J=7.5 Hz, 2H), 7.60 (d, J=7.4 Hz, 2H), 7.43-7.26 (m, 5H), 7.12 (t, J=5.2 Hz, 1H), 5.96 (d, J=7.0 Hz, 1H), 4.51-4.31 (m, 4H), 4.30-4.18 (m, 3H), 4.01 (s, 2H), 3.81 (dd, J=8.5, 3.3 Hz, 1H), 3.73-3.54

(m, 10H), 3.50-3.42 (m, 2H), 3.42-3.35 (m, 1H), 3.06-2.90 (m, 2H), 2.82 (s, 2H), 2.30 (t, J=7.6 Hz, 2H), 1.60 (m, 2H), 1.47 (s, 9H), 1.21-1.35 (m, 24H), 1.17 (s, 9H), 0.88 (t, 3H).
$^{13}$C NMR (101 MHz, CDCl$_3$) δ 173.60, 171.07, 169.95, 169.69, 143.72, 143.69, 141.26, 127.72, 127.07, 125.12, 119.97, 81.55, 73.97, 70.65, 70.53, 70.49, 70.27, 69.69, 68.94, 67.26, 62.83, 61.31, 54.44, 53.45, 47.08, 39.42, 34.68, 34.13, 31.91, 31.00, 29.67, 29.64, 29.60, 29.46, 29.34, 29.28, 29.14, 28.08, 27.36, 24.86, 22.67, 14.18.

NH$_2$-Cys(EtOC(O)C$_{15}$H$_{31}$)-Ser(OtBu)-NH (CH$_2$CH$_2$O)$_3$CH$_2$C(O)OtBu (24)

FmocNH-Cys(EtOC(O)C$_{15}$H$_{31}$)—Ser(OtBu)-NH (CH$_2$CH$_2$O)$_3$CH$_2$C(O)OtBu (0.22 mmol, 0.23 g) was dissolved in dry DCM (1 mL). Octanethiol (1.1 mmol, 0.19 mL) was added. DBU (22 µmol, 3.3 µL) was added and the mixture was stirred for 3 hours at RT under argon atmosphere. TLC analysis (EA) indicated completion of reaction. Celite was added and the DCM was evaporated in vacuo. The crude was purified by silica gel column chromatography (1:1 EA:Pnt→9:1 EA:MeOH+1% TEA). Compound 24 (0.20 mmol, 154 mg) was obtained with an 88% yield.
[α]$_D$: −1.1°
IR (cm$^{-1}$)=2923, 2852, 1734, 1647,
HRMS [M+H]$^+$: 792.53907 (measured), 792.54024 (calculated).
$^1$H NMR (400 MHz, CDCl$_3$) δ 8.10 (d, J=7.3 Hz, 1H), 7.09 (t, J=5.3 Hz, 1H), 4.42 (td, J=7.3, 4.2 Hz, 1H), 4.22 (t, J=6.8 Hz, 2H) 4.02 (s, 2H), 3.76 (dd, J=8.7, 4.2 Hz, 1H), 3.67-3.56 (dd, J=23.1, 3.7 Hz, 11H), 3.48 (t, J=4.8 Hz, 2H), 3.39 (t, J=8.1 Hz, 1H), 3.06 (dd, J=13.5, 4.0 Hz, 1H), 2.77 (dt, J=10.3, 4.1 Hz, 3H), 2.31 (t, J=7.5 Hz, 2H), 1.60 (m, J=14.4, 7.3 Hz, 3H), 1.48 (s, 9H), 1.26 (s, 24H), 1.20 (s, 9H), 0.88 (t, J=6.8 Hz, 3H)
$^{13}$C NMR (101 MHz, CDCl$_3$) δ 173.56, 170.18, 169.61, 81.60, 73.88, 70.66, 70.53, 70.29, 69.83, 68.95, 62.98, 61.57, 54.30, 52.93, 39.36, 37.86, 31.91, 30.64, 29.68, 29.64, 29.60, 29.46, 29.35, 29.27, 29.13, 28.11, 27.40, 24.89, 22.68, 14.13.

NH$_2$C(O)NH-Cys(EtOC(O)C$_{15}$H$_{31}$)-Ser(OtBu)-NH (CH$_2$CH$_2$O)$_3$CH$_2$C(O)OtBu 24 (0.18 mmol, 142 mg) was dissolved in dry DCM (10 mL). Isopropanol (3.5 mmol, 0.27 mL) was added. 85% (Trimethylsilyl)isocyanate (1.8 mmol, 0.28 mL) was added and the mixture was stirred overnight at RT under argon atmosphere. Celite was added and the DCM was evaporated in vacuo. The adsorbed crude was purified by silica gel column chromatography (8:2 EA:Pnt+1% TEA→95:5 EA:MeOH+1% TEA). Product (0.14 mmol, 0.12 g) was obtained with a 82% yield. R$_f$ 0.5 EA.
[α]$_D$: +10
IR (cm$^{-1}$)=2917, 2849, 1733, 1634
HRMS [M+H]$^+$: 835.54504 (measured), 835.54606 (calculated).
$^1$H NMR (400 MHz, CDCl$_3$) δ 7.56 (t, J=6.1 Hz, 2H), 6.35 (d, J=6.6 Hz, 1H), 5.54 (s, 2H), 4.51 (m, 2H), 4.22 (t, J=6.7 Hz, 2H), 4.02 (s, 2H), 3.82 (dd, J=8.9, 3.7 Hz, 1H), 3.73-3.55 (m, 11H), 3.45 (dd, J=8.9, 5.7 Hz, 1H), 3.36 (dt, J=12.7, 3.7 Hz, 1H), 2.95 (m, 2H), 2.79 (t, J=6.7 Hz, 2H), 2.31 (m, J=7.6 Hz, 2H), 1.65-1.55 (m, 2H), 1.48 (s, 9H), 1.35-1.21 (m, 24H), 1.16 (s, 9H), 0.88 (t, J=6.9 Hz, 3H).
$^{13}$C NMR (101 MHz, CDCl$_3$) δ 173.80, 171.34, 170.34, 169.86, 159.15, 82.09, 73.62, 70.69, 70.67, 70.37, 70.28, 69.89, 69.00, 62.91, 61.62, 54.07, 53.52, 39.62, 34.63, 34.21, 31.95, 30.85, 29.73, 29.70, 29.53, 29.39, 29.34, 29.21, 28.16, 27.43, 24.93, 22.72, 14.17

NH$_2$C(O)NH-Cys(EtOC(O)C$_{15}$H$_{31}$)-Ser(OH)—NH (CH$_2$CH$_2$O)$_3$CH$_2$C(O)OH (7)

NH$_2$C(O)NH-Cys(EtOC(O)C$_{15}$H$_{31}$)-Ser(OtBu)-NH (CH$_2$CH$_2$O)$_3$CH$_2$C(O)OtBu
(0.14 mmol, 0.11 g) was dissolved in dry DCM (2 mL). TFA (2 mL) was added and the mixture was stirred for 1 hour. The TFA was evaporated in vacuo. The crude was dissolved in DCM and dropped in a tube with Et$_2$O (35 mL). Compound 7 (0.10 mmol, 74 mg) was obtained with a 71% yield.
[α]$_D$: −2°
IR (cm$^{-1}$)=3282, 2917, 2849, 1729, 1638
HRMS [M+H]$^+$: 723.42011 (measured), 723.42086 (calculated).
$^1$H NMR (400 MHz, CDCl$_3$) δ 8.19 (d, J=5.7 Hz, 1H), 7.89 (s, 1H), 6.66 (s, 1H), 4.58 (s, 2H), 4.21 (m, 4H), 3.86 (d, J=29.0 Hz, 2H), 3.65 (dd, J=38.0, 20.2 Hz, 10H), 3.48 (m, 2H), 2.93 (s, 2H), 2.79 (t, J=6.2 Hz, 2H), 2.30 (t, J=7.6 Hz, 2H), 1.58 (m, 2H), 1.23 (m, 24H), 0.88 (t, J=6.7 Hz, 3H).
$^{13}$C NMR (101 MHz, CDCl$_3$) δ 173.99, 173.77, 172.33, 170.67, 160.19, 70.68, 70.45, 70.14, 69.61, 68.44, 63.02, 62.57, 55.65, 53.85, 39.66, 34.70, 34.28, 32.04, 30.83, 29.82, 29.78, 29.65, 29.48, 29.32, 25.00, 22.80, 14.24.

NH$_2$-DEVSGLEQLESIINFEKL-Resin Bound (25)

Preloaded leucine resin (0.05 mmol) was subjected to solid phase Fmoc peptide synthesis using standard Fmoc protected amino acid building block (NovaBiochem, 0.25 mmol, 5 eq), HCTU as an activating agent, and Fmoc cleavage as the final step.

NH$_2$-DEVSGLEQLESIINFEK($^{N3}$)L-Resin Bound (26)

26 was synthesized using the same procedure than 25 using Fmoc-azido norleucine instead of Fmoc-Lys(Boc) for the first coupling.

NH$_2$C(O)NH-Cys(EtOC(O)C$_{15}$H$_{31}$)-Ser(OH)—O (CH$_2$CH$_2$O)$_3$CH$_2$C(O)NH-DEVSGLEQLESIIN-FEKL-OH (8)

Resin 25 (12 µmol) was put in a syringe and suspended in NMP until resin appeared sufficiently swollen. 6 (12 µmol, 10 mg) was preactivated with HCTU (12 µmol, 5 mg) to form a 0.2M solution, which was added to 25. A solution of 1M DIPEA in NMP (12 µL) was added and the syringe was shaken for 15 min, after which 1M DIPEA in NMP (12 µL) was added again. The syringe was shaken overnight, when a Kaiser test indicated completion of reaction. The resin was washed with DCM (3×) after which a solution of TFA/TIS/H$_2$O (95/2, 5/2, 5) was added. The syringe was shaken for 75 min and the solution was dropped in Et$_2$O. After overnight precipitation and HPLC purification compound 8 (0.6 µmol, 1.7 mg) was obtained.
HRMS [(M+2H)/2]: 1385.23537 (measured), 1385.22598 (calculated).

NH$_2$C(O)NH-Cys(EtOC(O)C$_{15}$H$_{31}$)-Ser(OH)—NH (CH$_2$CH$_2$O)$_3$CH$_2$C(O)NH-DEVSGLEQLESIIN-FEKL-OH (9)

The procedure used to synthesize 8 was also used to obtain 9. 7 (48 µmol, 35 mg) was used instead of 6, thus 9 (1.5 µmol, 4.3 mg) was obtained.

HRMS [(M+2H)/2]:1384.74236 (measured), 1384.73397 (calculated).

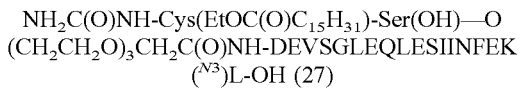
NH$_2$C(O)NH-Cys(EtOC(O)C$_{15}$H$_{31}$)-Ser(OH)—O(CH$_2$CH$_2$O)$_3$CH$_2$C(O)NH-DEVSGLEQLESIINFEK($^{N3}$)L-OH (27)

Resin 26 bound (20 µmol) was put in a syringe and suspended in NMP until resin appeared sufficiently swollen. 6 (20 µmol, 14 mg) was preactivated with HCTU (20 µmol, 8.3 mg) to form a 0.2 M solution, which was added to 26. A solution of 1M DIPEA in NMP (20 µL) was added and the syringe was shaken for 15 min, after which 1M DIPEA in NMP (20 µL) was added again. The syringe was shaken overnight, when a Kaiser test indicated completion of reaction. The resin was washed with DCM (3×) after which a solution of TFA/TIS/H$_2$O (95/2, 5/2, 5) was added. The syringe was shaken for 75 min and the solution was dropped in Et$_2$O. After overnight precipitation and HPLC purification compound 27 (1.4 µmol, 4.0 mg) was obtained.

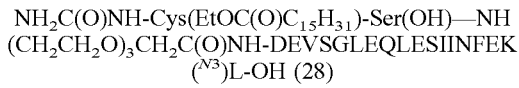
NH$_2$C(O)NH-Cys(EtOC(O)C$_{15}$H$_{31}$)-Ser(OH)—NH(CH$_2$CH$_2$O)$_3$CH$_2$C(O)NH-DEVSGLEQLESIINFEK($^{N3}$)L-OH (28)

The procedure used to synthesize 27 was also used to obtain 28. 7 (20 µmol, 14 mg) was used instead of 6, thus 28 (0.75 µmol, 2.09 mg) was obtained.

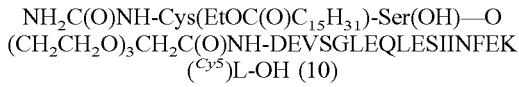
NH$_2$C(O)NH-Cys(EtOC(O)C$_{15}$H$_{31}$)-Ser(OH)—O(CH$_2$CH$_2$O)$_3$CH$_2$C(O)NH-DEVSGLEQLESIINFEK($^{Cy5}$)L-OH (10)

Compound 27 (0.3 µmol, 0.8 mg) was dissolved in dry DMSO (100 µL). Cy5-BCN (1.08 µmol, 0.9 mg) in dry DMSO (100 µL) was added to the solution. The reaction mixture was stirred at RT for 1 week. After HPLC purification, 10 (30 nmol, 1 mg) was obtained.
HRMS [(M+1H)/2]: 1792.97317 (measured), 1792.96897 (calculated).

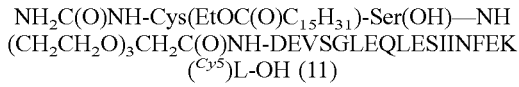
NH$_2$C(O)NH-Cys(EtOC(O)C$_{15}$H$_{31}$)-Ser(OH)—NH(CH$_2$CH$_2$O)$_3$CH$_2$C(O)NH-DEVSGLEQLESIINFEK($^{Cy5}$)L-OH (11)

Compound 28 (0.3 µmol, 0.8 mg) was dissolved in dry DMSO (100 µL). Cy5-BCN (0.36 µmol, 0.3 mg) in dry DMSO (100 µL) was added to the solution. The reaction mixture was stirred at RT for 1 week. After HPLC purification, 11 (0.1 µmol, 3.5 mg) was obtained.

HRMS [(M+1H)/2]:1791.47912 (measured), 1791.471375 (calculated).

In Vitro DC Maturation Assay

The D1 dendritic cell line is a growth factor-dependent immature spleen-derived DC line from C57BL/6 (H-2b) mice. D1 cells were cultured as described (Winzler, C.; Rovere, P.; Rescigno, M.; Granucci, F.; Penna, G.; Adorini, L.; Zimmermann, V. S.; Davoust, J.; Ricciardi-Castagnoli, P. Maturation stages of mouse dendritic cells in growth factor-dependent long-term cultures. J. Exp. Med. 1997, 185, 317-328). Test compounds were titrated in a 96-wells plate (Corning, Amsterdam, The Netherlands) in complete IMDM medium. Next, D1 cells were harvested, counted, and subsequently transferred to the 96-well plates containing the test compound titrations, using approximately 40 000 cells per well. After 24 h of incubation at 37° C., supernatant was taken from the wells for ELISA analysis (BioLegend, San Diego, CA) in which the amount of produced IL-12p40 was measured. After 48 h, the DCs were stained with a fluorescent antibody directed against CD86 (eBioscience, San Diego, CA) and analyzed by flow cytometry, acquiring 50 000 cells per sample.

HEK293-TLR2 Activation Assay

The HEK-TLR2 reporter cell line and HEK293 cells stably transfected with human TLR2 were obtained from Invivogen, Toulouse, France. HEK-TLR2 cells were cultured in complete IMDM medium, supplemented with 500 µg/mL Geneticin. Test compounds were titrated in a flat-bottom 96-well plate (Corning, Amsterdam, The Netherlands) in complete IMDM medium to which 20 000 HEK-TLR2 cells per well were added. After 48 h of incubation at 37° C., the supernatant was taken from the wells for ELISA analysis (BioLegend, San Diego, CA) to determine the amount of IL-8 that was produced as a measure for TLR2-mediated activation.

The data presented in this study indicates the utility of the compounds described as adjuvants for modulating immune responses. Furthermore it has been shown that the compounds of the present invention are more potent adjuvants than those currently available, and are still taken up into the cell when conjugated to other moieties, such as peptides.

While the present disclosure has been described with reference to certain examples, those skilled in the art will appreciate that various modifications, changes, omissions, and substitutions can be made without departing from the spirit of the disclosure. It is intended, therefore, that the compounds, conjugates, methods and related aspects be limited by the scope of the following claims. The features of any dependent claim may be combined with the features of any of the independent claims or other dependent claims.

The invention claimed is:

1. An adjuvant compound of Formula (I):

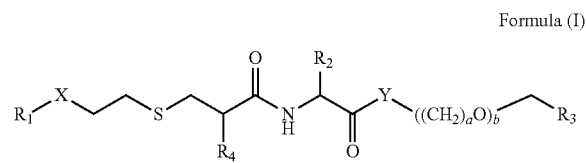

Formula (I)

or a pharmaceutically acceptable salt, or solvate thereof, wherein:

X is selected from —C(O)—O—, —O—C(O)—, —C(O)—, —C(O)—NH—, —NH—C(O)—, —NH—C(O)—O— and —O—C(O)—NH—;

Y is selected from —O—, —S— and —NH—;

a is 2;

b is 3;

$R_1$ is selected from a $C_{14-17}$ alkyl group;

$R_2$ is $C_{1-6}$ alkyl, which is substituted with —OH;

$R_3$ is selected from —C(O)—$OR_6$ and —C(O)—$NHR_6$, in which $R_6$ is a peptide or fragment thereof; and $R_4$ is —NH—C(O)—$NH_2$.

2. The compound of claim 1, wherein
a) X is selected from —C(O)—O— and —C(O)—NH—;
b) $R_1$ is $C_{15}$ alkyl;
c) $R_2$ is hydroxymethyl;
or
d) the compound comprises two or more of features a) to c) above.

3. The compound of claim 1, wherein the compound is a TLR2 agonist.

4. The compound of claim 1, wherein the peptide comprises a peptide antigen or wherein the peptide fragment comprises an antigenic fragment of the peptide.

5. A method of modulating an immune response in a subject in need thereof, comprising administering an effective amount of the compound of claim 1 to the subject.

6. The method of claim 5, wherein the immune response is induced or enhanced.

7. The method of claim 4, wherein the subject has or is susceptible to cancer, an infectious disease, a non-autoimmune metabolic or degenerative disease or an atopic disease, and wherein optionally the cancer is caused by a viral infection selected from HBV, HCV, HPV, Epstein-Barr virus (EBV), Merkel cell polyomavirus, Kaposi's sarcoma-associated virus (HHV-8).

8. The method of claim 5, wherein the compound of claim 1 is administered in combination with an antigen to which the immune response is required.

9. The method of claim 8, wherein the subject has cancer and the antigen to which the immune response is required is a subject-derived tumour antigen, and optionally wherein the subject-derived tumour antigen is identified through biopsy and genome sequencing to identify mutant proteins within the subject's mutanome.

10. A method of treating cancer, comprising administering to a subject in need thereof a compound of claim 1 in combination with a therapeutic agent.

11. The method of claim 10, wherein the compound of claim 1 is administered in combination with an antigen to which the immune response is required.

12. The method of claim 11, wherein the antigen to which the immune response is required is a subject-derived tumour antigen, and optionally wherein the subject-derived tumour antigen is identified through biopsy and genome sequencing to identify mutant proteins within the subject tumour's mutanome.

13. A method of treating a viral infection or bacterial infection, comprising administering to a subject in need thereof the compound of claim 1 in combination with a therapeutic agent.

14. A kit-of-parts, comprising:
the compound of claim 1; and
a therapeutic agent selected from a chemotherapeutic agent, an anti-inflammatory agent, an anti-viral agent, and an antigen to which an immune response is required.

* * * * *